US009989519B1

(12) United States Patent
Bhoopathy et al.

(10) Patent No.: US 9,989,519 B1
(45) Date of Patent: Jun. 5, 2018

(54) METHOD FOR DETERMINING IN VITRO BIOEQUIVALENCE OF A SUCRALFATE SUSPENSION SAMPLE TO A SUCRALFATE SUSPENSION REFERENCE LISTED DRUG (RLD)

(71) Applicant: Clayton Pharmaceuticals, LLC, Exton, PA (US)

(72) Inventors: Siddhartha Bhoopathy, Malvern, PA (US); Indranil Nandi, New Providence, NJ (US); Ami C. Patel, Doylestown, PA (US); Ismael J. Hidalgo, Exton, PA (US)

(73) Assignee: Clayton Pharmaceuticals, LLC, Exton, PA (US)

( * ) Notice: Subject to any disclaimer, the term of this patent is extended or adjusted under 35 U.S.C. 154(b) by 0 days. days.

(21) Appl. No.: 15/587,295

(22) Filed: May 4, 2017

(51) Int. Cl.
*G01N 33/50* (2006.01)
(52) U.S. Cl.
CPC .................. *G01N 33/502* (2013.01)
(58) Field of Classification Search
None
See application file for complete search history.

(56) References Cited

PUBLICATIONS

Jiang X., Yang Y., Stier E. (2014) Bioequivalence for Drug Products Acting Locally Within Gastrointestinal Tract. In: Yu L., Li B. (eds) FDA Bioequivalence Standards. AAPS Advances in the Pharmaceutical Sciences Series, vol. 13. Springer, New York, NY.*
Statistical Approaches to Establishing Bioequivalence, Guidance for Industry (2001), available at https://www.fda.gov/downloads/drugs/guidances/ucm070244.pdf.*
Carafate Suspension Product PIL. (Exhibit 1).
https://www.fda.gov/downloads/Drugs/GuidanceComplianceRegulatoryInformation/Guidances/UCM070246.pdf(Exhibit 2).
Cutting, K.F., Wound exudate: composition and functions. British Journal of community nursing. Feb. 2003. pp. 4-9. (Exhibit 3).
Ito, Y., Onada, Y., Nakamura, S. Tagawa, K., Fukushima, T., Suguwara, Y., and Takaiti, O. Effects of new anti-ulcer drug ecabet sodium (TA-2711) on pepsin activity. II. Interaction with substrate protein, Japan J. Pharmacol., 62, 175-181; 1993 (Exhibit 4).
Duane, W. and Wiegand, D. Mechanism by which bile salt disrupts the gastric mucosal barrier in the dog. The Journal of clinical investigation, vol. 66, Nov. 1980 1044-1049 (Exhibit 5).
Graham, D.Y., Sackman, J.W., Giesing, D. H., and Runser, D. J.. In Vitro Adsorption of Bile Salts and Aspirin to Sucralfate. Digestive diseases and sciences, vol. 29, No. 5 (May 1984), pp. 402-406 (Exhibit 6).
Ito, Y., et al. (1993). Effects of the new anti-ulcer drug Ecabet Sodium (TA-2711) on pepsin activity: I. Inactivation of enzyme protein. Japanese Journal of Pharmacology, 62: 169-174. (Exhibit 7).
Samloff, I. M., & O'Dell, C. (1985). Inhibition of peptic activity by Sucralfate. The American Journal of Medicine, 79 (suppl 2C): 15-18. (Exhibit 8).
Sigma-Aldrich (n.d.). Technical bulletin for Protease Colorimetric Detection Kit (Product Code PC0100). Retrieved from http://www.sigmaaldrich.com/content/dam/sigma-aldrich/docs/Sigma/Bulletin/pc0100bul.pdf. (Exhibit 9).
Thomas, K., et al. (2004). A multi-laboratory evaluation of a common in vitro pepsin digestion assay protocol used in assessing the safety of novel proteins. Regulatory Toxicology and Pharmacology, 39: 87-98. (Exhibit 10).
Furukawa, O., Matsui, H., & Suzuki, N. (1997). Effects of Sucralfate and its components on acid- and pepsin-induced damage to rat gastric epithelial cells. Japanese Journal of Pharmacology, 75: 21-25. (Exhibit 11).
Okabe, S., and Amagase, K. An overview of acetic acid ulcer models—The history and state of the art of peptic ulcer research. Biol. Pharm. Bull. 28(8) 1321-1341. 2005 (Exhibit 12).
Dobrozsi, D.J., Smith, R.L., Sakr, A.A. Comparative mucoretention of Sucralfate suspensions in an everted rat esophagus model. International Journal of Pharmaceutics 189. 81-89. 1999. (Exhibit 13).
Tang, A. S., Chikhale, P.J., Shah, P., Borchardt, R., Utilization of a human intestinal epithelial cell culture system (Caco-2) for evaluating cytoprotective agents. (Exhibit 14).

* cited by examiner

*Primary Examiner* — Robert J Yamasaki
(74) *Attorney, Agent, or Firm* — Adriano & Associates

(57) ABSTRACT

The invention provides methods for determining in vitro bioequivalence of a sucralfate suspension sample to a sucralfate suspension RLD.

23 Claims, 17 Drawing Sheets

US 9,989,519 B1

METHOD FOR DETERMINING IN VITRO BIOEQUIVALENCE OF A SUCRALFATE SUSPENSION SAMPLE TO A SUCRALFATE SUSPENSION REFERENCE LISTED DRUG (RLD)

Throughout this application various publications are referenced. The disclosures of these publications in their entireties are hereby incorporated by reference into this application in order to more fully describe the state of the art to which this invention pertains.

FIELD OF THE INVENTION

The present invention relates to methods for determining in vitro bioequivalence of a sucralfate suspension sample to a sucralfate suspension RLD.

BACKGROUND OF THE INVENTION

A peptic ulcer is a focal mucosal defect with inflammatory cell infiltration and coagulation necrosis extending through the muscularis mucosae. The overall concept of the pathophysiology of peptic ulcer disease (PUD) is that there is a disturbed equilibrium between the aggressive and protective factors, with a very complex interplay between the factors. Peptic ulcers, characterized by a damaged gastric mucosal barrier, tend to occur within the section of the gastrointestinal (GI) tract that is in contact with gastric juice containing acid and pepsin. The gastric mucosal barrier is the feature of the stomach that allows it to safely contain the gastric acid required for digestion. The predilection sites for ulcers are the vicinity of mucosal junctions such as the transitional zone between the esophageal and gastric mucosa and the gastro-duodenal junction. PUD is commonly associated with gastritis and it is generally accepted that colonization by the bacterium *H. pylori* is causatively related to gastritis associated with PUD.

Carafate® suspension (Sucralfate suspension) is available in the United States as an oral suspension. It was approved in 1993 for the treatment of active duodenal ulcers. It is also widely used for the treatment of PUD, gastritis due to gastroesophageal reflux disease (GERD), irritable bowel syndrome (IBS), non-erosive reflux disorder (NERD) and functional dyspepsia. Sucralfate may also be used to prevent recurrent ulcers after healing of the ulcer has been achieved. It is also used to relieve or prevent ulcers caused by non-steroidal anti-inflammatory drugs (NSAIDs).

The mechanism of action of sucralfate is not fully understood and several possible mechanisms have been suggested. In general, it is widely believed that sucralfate exerts its anti-ulcer activity by forming an ulcer-adherent complex with the proteinaceous exudate at the ulcer site, thus covering the ulcer site and protecting it against further attack by aggressive factors such as acid, pepsin and bile salts.

A need remains for an oral Sucralfate suspension that is safe, efficacious and cost-efficient generic drug product of Sucralfate suspension that can be developed and made available to the patient population. This discovery addresses that need by identifying sucralfate suspensions that are bioequivalents of sucralfate suspension RLD.

SUMMARY OF THE INVENTION

The present invention provides, for the first time, methods for determining in vitro bioequivalence of a sucralfate suspension sample to a sucralfate suspension RLD comprising contacting the sucralfate suspension sample with a bile acid, bile salt and/or conjugated bile acid or a combination thereof, so as to permit sucralfate-bile interaction, quantifying the interaction so as to obtain quantified values of the interaction and comparing said values to reference values for the sucralfate suspension RLD.

The present invention additionally comprises contacting the sucralfate suspension sample with a cell culture system in the presence of a Non-Steroidal Anti-Inflammatory Drug (NSAID) or a nonselective inhibitor of cyclooxygenase (COX) 1 and 2 so as to inhibit cell damage induced by the NSAID or nonselective inhibitor of COX 1 and 2 in the cell culture system, quantifying the cell damage so as to obtain quantified value(s) for the sucralfate suspension sample and comparing the said value(s) to reference values for the sucralfate suspension RLD.

The invention further provides a method for obtaining a sucralfate suspension sample that is a bioequivalent of a sucralfate suspension RLD by determining in vitro bioequivalence.

The invention also provides a method for reducing or alleviating the symptoms associated with an ulcer in a patient suffering from the ulcer comprising administering to the patient an effective amount of any of the sucralfate suspension samples identified by the methods herein thereby reducing or alleviating the symptoms associated with an ulcer in the patient.

The biological outcome of the formulation depends on the similarity of the generic formulation with that of the RLD in Pharmaceutical Equivalence (PE) and Bioequivalence (BE). Taking into consideration, the complex nature of the Active Pharmaceutical Ingredient (API; i.e. Sucralfate), the locally acting nature of Sucralfate, and the multiple postulated modes of action of Sucralfate, establishing PE alone is insufficient to establish Therapeutic Equivalence (TE) of this product. Establishing BE via a clinical endpoint study as previously recommended by the USFDA has not been a successful approach to date. The current invention proposes an in-vitro based strategy that relies on orthogonal measurements of action (association with bile acids) and effect (Cytoprotection) to characterize product performance and demonstrate TE of the test product to the RLD.

DETAILED DESCRIPTION OF THE INVENTION

Figure 1:
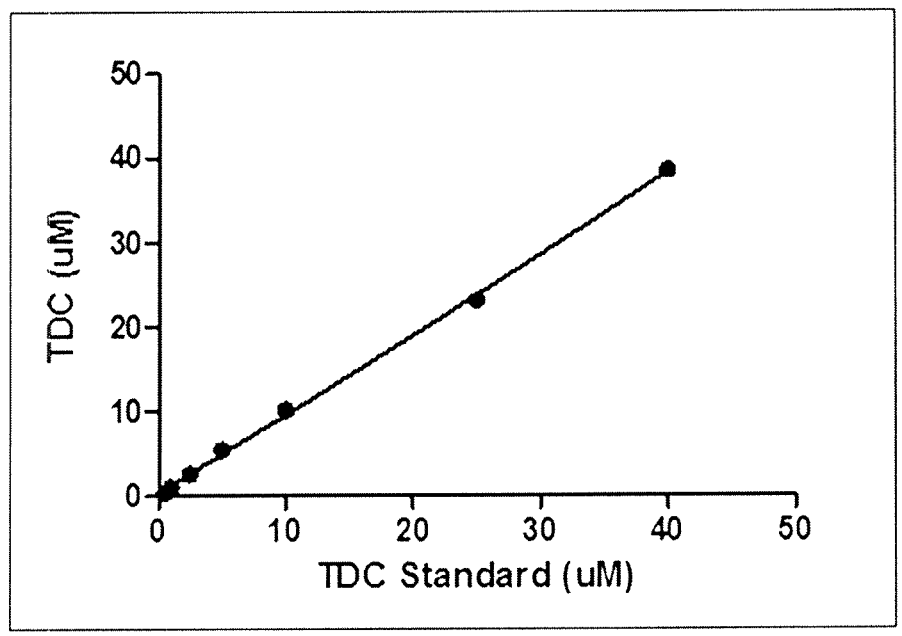
FIG. 1. Representative standard curve for TDC detection.

All scientific and technical terms used in this application have meanings commonly used in the art unless otherwise specified. As used in this application, the following words or phrases have the meanings specified.

Sucralfate is an hydrous basic aluminium salt of sucrose octasulfate (e.g., CAS Number: 54182-58-0; U.S. Pharmacopeial USP 35 monograph,). In one embodiment, it has the chemical structure of:

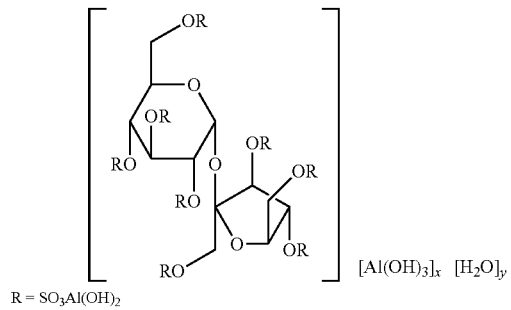

R = SO$_3$Al(OH)$_2$

In another embodiment, sucralfate has a chemical formula Al$_8$(OH)$_{16}$(C$_{12}$H$_{14}$O$_{35}$S$_8$)[Al(OH)$_3$]$_x$[H$_2$O]$_y$, in which x=8 to 10, and y=22 to 31. Sucralfate may contain the equivalent of not less than about 30.0 percent and not more than about 38.0 percent of sucrose octasulfate (C$_{12}$H$_{14}$O$_{35}$S$_8$). Typically, between about 15.5% and about 18.5% of aluminum may be found in Sucralfate.

The term "RLD" or RLD refers to an approved drug product to which new generic versions are compared to show that they are bioequivalent. In one example, a Sucralfate Suspension RLD is Carafate® (Forest Laboratories, Inc.; Application Number: N019183; approval date: Dec. 16, 1993) which is a RLD in the United States and can be found in U.S. FDA's Orange Book.

A "suspension" is a liquid dosage form that contains solid particles dispersed in a liquid vehicle. These solid particles include drug substance, and may include excipients such as swellable polymeric muco-adhesives such as celluloses. In addition to the solid particles and vehicle, the suspension may include excipients, such as microcrystalline cellulose, colloidal silicon dixodie, methyl cellulose as supending agents, glycerin and sorbitol as bodying agents, simethicone as anti-foaming agent, methyl paraben as a preservative, food colorant and flavoring. Vehicle may be aqueous, non-aqueous or a mixture of both. In one embodiment, the vehicle is an aqueous solution or water. Merely by way of example, each 10 mL of a Sucralfate suspension may contain 1 g±10% of Sucralfate.

The term "acid" refers to a chemical compound that, when dissolved in water, gives a solution with a pH less than 7. The "acid" can be organic. It can have a pKa in the range of e.g., 2-5. Examples of acids suitable for the invention include, but are not limited to, bile acid, tartaric acid, adipic acid, succinic acid, citric acid, benzoic acid, acetic acid, ascorbic acid, edetic acid, fumaric acid, lactic acid, malic acid, oleic acid, sorbic acid, stearic acid, palmitic and boric acid or mixtures thereof.

The term "bile acid" may be any of allocholic acid (3alpha,7alpha,12alpha-trihydroxy-5alpha-cholanoic acid; CAS: 2464-18-8), 5alpha-deoxycholic acid (3alpha,12alpha-dihydroxy-5alpha-cholan-24-oic acid), bitocholic acid, chenodeoxycholic acid (3alpha,7alpha-dihydroxy-5beta-cholan-24-oic acid; CAS: 474-25-9), cholic acid (3alpha, 7alpha, 12alpha-trihydroxy-5beta-cholan-24-oic acid; CAS: 81-25-4), deoxycholic acid (3alpha, 12alpha-dihydroxy-5beta-cholanic acid; CAS: 83-44-3), glycochenodeoxycholic acid (2-[[(4R)-4-[(3R,5S,7R,8R,9S,10S,13R,14S, 17R)-3,7-dihydroxy-10,13-dimethyl-2,3,4,5,6,7,8,9,11,12, 14,15,16,17-tetradecahydro-1H-cyclopenta[a]phenanthren-17-yl]pentanoyl]amino]acetic acid; CAS No.: 640-79-9), glycocholic acid (3alpha,7alpha,12alpha-trihydroxy-5beta-cholan-24-oylglycine; CAS: 475-31-0), hyocholic acid (3alpha,6alpha,7alpha-trihydroxy-5beta-cholan-24-oic acid; CAS: 547-75-1), hyodeoxycholic acid (3α,6α-Dihydroxy-5β-cholan-24-oic acid; CAS: 83-49-8), isochenodeoxycholic acid (3beta,7alpha-dihydroxy-5beta-cholanic acid; CAS: 566-24-5), 3 beta, 12alpha-Dihydroxy-5beta-cholanoic acid (CAS: 570-63-8), isolithocholic acid (3beta-Hydroxy-5beta-cholan-24-oic acid; CAS: 1534-35-6), isoursodeoxycholic acid (3beta,7beta-dihydroxy-5beta-cholan-24-oic acid; CAS: 78919-26-3), 12-epideoxycholic acid, lithocholic acid (3alpha-hydroxy-5beta-cholanic acid; CAS: 434-13-9), alpha-muricholic acid (3alpha,6beta,7alpha-trihydroxy-5beta-cholan-24-oic acid; CAS: 2393-58-0), beta-muricholic acid (3alpha,6beta,7beta-trihydroxy-5beta-cholan-24-oic acid; CAS: 2393-59-1), omega-muricholic acid, murideoxycholic acid (3alpha,6beta-dihydroxy-5beta-cholanic acid), beta-phocaecholic acid (CAS: 105369-89-9), taurochenodeoxycholic acid (2-[[(4R)-4-[(3R,5S,7R,8R,9S, 10S,13R,14S,17R)-3,7-dihydroxy-10,13-dimethyl-2,3,4,5, 6,7,8,9,11,12,14,15,16,17-tetradecahydro-1H-cyclopenta[a] phenanthren-17-yl]pentanoyl]amino]ethanesulfonic acid; CAS No.: 516-35-8), taurocholic acid (2-[[(4R)-4-[(3R,5S, 7R,8R,9S,10S,12S,13R,14S,17R)-3,7,12-trihydroxy-10,13-dimethyl-2,3,4,5,6,7,8,9,11,12,14,15,16,17-tetradecahydro-1H-cyclopenta[a]phenanthren-17-yl]pentanoyl]amino] ethanesulfonic acid; CAS No.: 81-24-3), taurodeoxycholic acid (2-(((3alpha,5beta, 12alpha)-3,12-dihydroxy-24-oxocholan-24-yl)amino)-ethanesulfonic acid; CAS No.: 516-50-7), ursocholic acid (3 alpha,7beta, 12alpha-trihydroxy-5beta-cholan-24-oic acid; CAS: 2955-27-3), ursodeoxycholic acid (3alpha,7beta-dihydroxy-5beta-cholan-24-oic acid; CAS: 128-13-2), and vulpecholic acid (1alpha,3alpha,7alpha-trihydroxy-5beta-cholan-24-oic acid; CAS: 107368-95-6).

The bile acid may be "unconjugated bile acid" such as cholic acid or chenodeoxycholic acid.

A "conjugated bile acid" may be obtained from bile acid or bile salt. For example, cholic acid or chenodeoxycholic acid may be conjugated with taurine or glycine to produce glycocholic acid or taurocholic acid in the case of cholic acid or glycochenodeoxycholic acid or taurochenodeoxycholic acid in the case of chenodeoxycholic acid.

A "conjugate base of a bile acid" is a bile acid anion. Bile acid anion may be selected from, but not limited to, allocholate, 5alpha-deoxycholate, bitocholate, chenodeoxycholate, cholate, deoxycholate, glycochenodeoxycholate, glycocholate, hyocholate, hyodeoxycholate, isochenodeoxycholate, 3beta, 12alpha-Dihydroxy-5beta-cholanoate, isolithocholate, isoursodeoxycholate, 12-epideoxycholate, lithocholate, alpha-muricholate, beta-muricholate, omega-muricholate, murideoxycholate, beta-phocaecholate, taurochenodeoxycholate, taurocholate, taurodeoxycholate, ursocholate, ursodeoxycholate, and vulpecholate and a combination thereof. Bile acid is a conjugate acid of bile acid anion. A "conjugate base of a bile acid" may be obtained following dissolution of a bile acid or bile salt in an aqueous solution. For example, taurodeoxycholate (TDC) may be obtained following dissolution of taurodeoxycholic acid (2-(((3alpha,5beta, 12alpha)-3,12-dihydroxy-24-oxo-cholan-24-yl)amino)-ethanesulfonic acid; CAS No.: 516-50-7) or sodium taurodeoxycholate (CAS No.: 1180-95-6) in an aqueous solution. A bile salt may be a salt of a bile acid, such as for example, a sodium salt of a bile acid.

"Adsorption of bile acids to Sucralfate" used in the context of the invention refers to a binding interaction between Sucralfate as a solid and bile acid or bile salt dissolved in a solution.

"Binding of Sucralfate to bile acid" may be binding of Sucralfate to bile acid or to a conjugated bile acid.

The term "effective amount" means an amount of a compound/composition according to the present invention effective in producing the desired therapeutic effect.

The term "about" when used in connection with percentages means+/−1.00%.

The "upper GI tract" refers to the portion closest to the stomach and includes the esophagus, stomach and duodenum.

The term "treating" a disease or condition, means to manage a disease or condition with the pharmaceutical formulation of the invention. Treatment can decrease the symptoms of a disease or condition, reduce the severity of a disease or condition, alter the course of disease progression or condition, ameliorate and/or cure a disease or condition. The disease or condition may include but not limited to an ulcer, such as active duodenal ulcer and peptic ulcer disease (PUD), gastritis due to gastroesophageal disease (GERD), irritable bowel syndrome (IBS) non-erosive reflex disorder (NERD) and functional dyspepsia (FD).

The term "bioequivalence" refers to the absence of a significant difference in the rate and extent to which the active ingredient or active moiety in pharmaceutical equivalents or pharmaceutical alternatives becomes available at the site of drug action when administered at the same molar dose under similar conditions in an appropriately designed study.

It would be clear to one skilled in the art that in some embodiments, the active ingredient or active moiety in pharmaceutical equivalents or pharmaceutical alternatives may become available at the site of drug action when administered at the same amount or dose under similar conditions.

The term "in vitro bioequivalence" refers to an in vitro approach to demonstrating bioequivalence through a combination of in vitro binding studies and bioassays that support the postulated modes of action. For example, a test product formulation may be developed which is qualitatively and quantitatively the same or essentially the same as the RLD with respect to active and inactive ingredients. The critical material attributes and process parameters are optimized until similarity of the test product in formulation function and in the bioassays with the RLD product is achieved. With greater sampling (within a particular lot and between multiple lots of a test product and/or RLD product), there is greater confidence that the "in vitro bioequivalence" is reflective of the in vivo "bioequivalence" to ensure and establish a product efficacy and a therapeutic equivalence without resorting to a three-arm, placebo-controlled, in-vivo clinical endpoint study.

METHODS OF THE INVENTION

The invention provides a method of determining in vitro bioequivalence of a Sucralfate suspension sample to a Sucralfate Suspension RLD, based on a combination of in vitro binding studies and bioassays that support the postulated modes of action. The method comprises in vitro binding of Sucralfate to bile acid(s) and in vitro bioassay for Sucralfate-mediated inhibition of cell damage by a Non-Steroidal Anti-Inflammatory Drug (NSAID) or a nonselective inhibitor of cyclooxygenase (COX) 1 and 2 in a cell culture system. Comparison of the effectiveness of a Sucralfate Suspension sample to that of a Sucralfate Suspension RLD in the combination of in vitro binding study and bioassay is used to establish in vitro bioequivalence of the Sucralfate Suspension sample to the Sucralfate Suspension RLD.

The present invention provides, for the first time, methods for determining in vitro bioequivalence of a sucralfate suspension sample to a sucralfate suspension RLD comprising contacting the sucralfate suspension sample with a bile acid, bile salt and/or conjugated bile acid or a combination thereof, so as to permit sucralfate-bile interaction, quantifying the interaction so as to obtain quantified values of the interaction and comparing said values to reference values for the sucralfate suspension RLD.

The present invention additionally comprises contacting the sucralfate suspension sample with a cell culture system in the presence of a Non-Steroidal Anti-Inflammatory Drug (NSAID) or a nonselective inhibitor of cyclooxygenase (COX) 1 and 2 so as to inhibit cell damage induced by the NSAID or nonselective inhibitor of COX 1 and 2 in the cell culture system, quantifying the cell damage so as to obtain quantified value(s) for the sucralfate suspension sample and comparing the said value(s) to reference values for the sucralfate suspension RLD.

The reference values for the sucralfate suspension RLD to be used in comparing the sucralfate-bile interaction are derived from a set of values obtained from quantifying the sucralfate-bile interaction for 2 or more lots of the sucralfate suspension RLD; wherein sucralfate-bile interaction is interaction between sucralfate and bile acid, bile salt and/or 3 conjugated bile acid or a combination thereof; wherein the reference values of the sucralfate suspension RLD to be used in comparing the cell damage are derived from a set of values obtained from quantifying the reduction in cell damage for two (2) or more lots of the sucralfate suspension RLD; and wherein the sucralfate suspension sample is to have said in vitro bioequivalence to a sucralfate suspension RLD when the values determined for the sucralfate suspension sample are within the reference values for the sucralfate suspension RLD.

Suitable examples of bile acids includes any of, but not limited to, allocholic acid (3alpha,7alpha,12alpha-trihydroxy-5alpha-cholanoic acid; CAS: 2464-18-8), 5alpha-deoxycholic acid (3alpha,12alpha-dihydroxy-5alpha-cholan-24-oic acid), bitocholic acid, chenodeoxycholic acid (3alpha,7alpha-dihydroxy-5beta-cholan-24-oic acid; CAS: 474-25-9), cholic acid (3alpha,7alpha,12alpha-trihydroxy-5beta-cholan-24-oic acid; CAS: 81-25-4), deoxycholic acid (3alpha,12alpha-dihydroxy-5beta-cholanic acid; CAS: 83-44-3), glycochenodeoxycholic acid (2-[[(4R)-4-[(3R,5S,7R,8R,9S,10S,13R,14S,17R)-3,7-dihydroxy-10,13-dimethyl-2,3,4,5,6,7,8,9,11,12,14,15,16,17-tetradecahydro-1H-cyclopenta[a]phenanthren-17-yl]pentanoyl]amino]acetic acid; CAS No.: 640-79-9), glycocholic acid (3alpha,7alpha,12alpha-trihydroxy-5beta-cholan-24-oylglycine; CAS: 475-31-0), hyocholic acid (3alpha,6alpha,7alpha-trihydroxy-5beta-cholan-24-oic acid; CAS: 547-75-1), hyodeoxycholic acid (3α,6α-Dihydroxy-5β-cholan-24-oic acid; CAS: 83-49-8), isochenodeoxycholic acid (3beta,7alpha-dihydroxy-5beta-cholanic acid; CAS: 566-24-5), 3beta, 12alpha-Dihydroxy-5beta-cholanoic acid (CAS: 570-63-8), isolithocholic acid (3beta-Hydroxy-5beta-cholan-24-oic acid; CAS: 1534-35-6), isoursodeoxycholic acid (3beta,7beta-dihydroxy-5beta-cholan-24-oic acid; CAS: 78919-26-3), 12-epideoxycholic acid, lithocholic acid (3alpha-hydroxy-5beta-cholanic acid; CAS: 434-13-9), alpha-muricholic acid (3alpha,6beta,7alpha-trihydroxy-5beta-cholan-24-oic acid; CAS: 2393-58-0), beta-muricholic acid (3alpha,6beta,7beta-trihydroxy-5beta-cholan-24-oic acid; CAS: 2393-59-1), omega-muricholic acid, murideoxycholic acid (3alpha,6beta-dihydroxy-5beta-cholanic acid), beta-phocaecholic acid (CAS: 105369-89-9), taurochenodeoxycholic acid (2-[[(4R)-4-[(3R,5S,7R,8R,9S,10S,13R,14S,17R)-3,7-dihydroxy-10,13-dimethyl-2,3,4,5,6,7,8,9,11,12,14,15,16,17-tetradecahydro-1H-cyclopenta[a]phenanthren-17-yl]pentanoyl]amino]ethanesulfonic acid; CAS No.: 516-35-8), taurocholic acid (2-[[(4R)-4-[(3R,5S,7R,8R,9S,10 S,12S,13R,14S,17R)-3,7,12-trihydroxy-10,13-dimethyl-2,3,4,5,6,7,8,9,11,12,14,15,16,17-tetradecahydro-1H-cyclopenta[a]phenanthren-17-yl]pentanoyl]amino]ethanesulfonic acid; CAS No.: 81-24-3), taurodeoxycholic acid (2-(((3alpha,5 beta, 12alpha)-3,12-dihydroxy-24-oxocholan-24-yl)amino)-ethanesulfonic acid; CAS No.: 516-50-7), ursocholic acid (3alpha,7beta, 12alpha-trihydroxy-5beta-cholan-24-oic acid; CAS: 2955-27-3), ursodeoxycholic acid (3alpha,7beta-dihydroxy-5beta-cholan-24-oic acid; CAS: 128-13-2), and vulpecholic acid (1alpha,3alpha,7alpha-trihydroxy-5beta-cholan-24-oic acid; CAS: 107368-95-6) or a combination thereof.

In one embodiment, the bile salt is salt of a bile acid. In another embodiment, the bile salt is sodium salt of a bile acid. In another embodiment, the bile salt is potassium salt of a bile acid.

In one embodiment, the bile acid is selected from the group consisting of glycocholic acid (3alpha,7alpha,12alpha-trihydroxy-5beta-cholan-24-oylglycine; CAS No.: 475-31-0), glycochenodeoxycholic acid (2-[[(4R)-4-[(3R,5S,7R,8R,9S,10S,13R,14S,17R)-3,7-dihydroxy-10,13-dimethyl-2,3,4,5,6,7,8,9,11,12,14,15,16,17-tetradecahydro-1H-cyclopenta[a]phenanthren-17-yl]pentanoyl]amino]acetic acid; CAS No.: 640-79-9), and taurodeoxycholic acid (2-(((3alpha,5beta, 12alpha)-3,12-dihydroxy-24-oxocholan-24-yl)amino)-ethanesulfonic acid; CAS No.: 516-50-7) or a combination thereof. In another embodiment, the bile acid is or comprises a taurodeoxycholic acid (2-(((3alpha,5beta, 12alpha)-3,12-dihydroxy-24-oxocholan-24-yl)amino)-ethanesulfonic acid; CAS No.: 516-50-7).

In one embodiment, the bile acid is a conjugate base of a bile acid. In another embodiment, the conjugate base of a bile acid is selected from the group consisting of glycocholate, glycochenodeoxycholate, taurochenodeoxycholate and taurodeoxycholate or a combination thereof. In yet another embodiment, the conjugate base of a bile acid is or comprises taurodeoxycholate.

In one embodiment, the bile acid is an unconjugated bile acid or bile acid not conjugated to glycine or taurine. In another embodiment, the unconjugated bile acid is selected from the group consisting of allocholic acid, allodeoxycholic acid, bitocholic acid, chenodeoxycholic acid, cholic acid, deoxycholic acid, hyodeoxycholic acid, isochenodoxycholic acid, 3β,12α-dihydroxy-5β-cholanoic acid, isolithocholic acid, isoursodeoxycholic acid, 12-epideoxycholic acid, lithocholic acid, α-muricholic acid, β-muricholic acid, ω-muricholic acid, murideoxycholic acid, β-phocaecholic acid, ursocholic acid, ursodeoxycholic acid, vulpecholic acid, and hyocholic acid.

In one embodiment, the bile acid is a conjugated bile acid. In another embodiment, the conjugated bile acid is selected from the group consisting of glycocholate, glycochenodeoxycholate, taurochenodeoxycholate and taurodeoxycholate or a combination thereof. In yet another embodiment, the conjugated bile acid is or comprises taurodeoxycholate.

In one embodiment, the conjugated bile acid is any of allocholic acid, allodeoxycholic acid, bitocholic acid, chenodeoxycholic acid, cholic acid, deoxycholic acid, hyodeoxycholic acid, isochenodoxycholic acid, 3β,12α-dihydroxy-5β-cholanoic acid, isolithocholic acid, isoursodeoxycholic acid, 12-epideoxycholic acid, lithocholic acid, α-muricholic acid, β-muricholic acid, ω-muricholic acid, murideoxycholic acid, β-phocaecholic acid, ursocholic acid, ursodeoxycholic acid, vulpecholic acid or hyocholic acid, conjugated to a glycine or a taurine.

In one embodiment, the bile salt is a bile acid salt or salt of a conjugate base of a bile acid. In another embodiment, the bile salt comprises a bile acid salt or comprises a conjugate base of a bile acid and a cation selected from the group consisting of an alkali metal, alkaline earth metal, transition metal, other metal, ammonium, amine and quaternary ammonium. Suitable examples of the alkali metal can be any from the group consisting of lithium, sodium, potassium, rubidium and cesium. Suitable examples of the alkaline earth metal can be any selected from the group consisting of beryllium, magnesium, calcium, strontium and barium. Suitable examples of the transition metal can be any selected from the group consisting of chromium, molybdenum, manganese, iron, cobalt, nickel, copper, silver, gold, zinc and cadmium. Suitable examples of the amine can be any selected from the group consisting of methylamine, methoxylamine, methylenediamine, bromoethylamine, chloroethylamine, fluoroethylamine, dimethylamine, ethylenediamine, diethylamine, cystamine, aniline, nitro-benzenediamine, phenylenediamine, tris(2-chloroethyl)amine, tromethamine, ethanolamine, diethanolamine and triethanolamine. Suitable examples of the quaternary ammonium can be any selected from the group consisting of tetramethylammonium, tetrabutylammonium, tetraethylammonium, triethylmethylammonium and tributylmethylammonium. In one embodiment, the bile salt or bile acid salt is a sodium salt of a bile acid. In another embodiment, the bile salt or bile acid salt is a potassium salt of a bile acid. In another embodiment, the bile salt or bile acid salt is or comprises a sodium taurodeoxycholate (e.g., CAS No.: 1180-95-6).

In another embodiment, the bile salt comprises a conjugated bile acid and a cation selected from the group consisting of an alkali metal, alkaline earth metal, transition metal, other metal, ammonium, amine and quaternary ammonium. Suitable examples of the alkali metal can be any from the group consisting of lithium, sodium, potassium, rubidium and cesium. Suitable examples of the alkaline earth metal can be any selected from the group consisting of beryllium, magnesium, calcium, strontium and barium. Suitable examples of the transition metal can be any selected from the group consisting of chromium, molybdenum, manganese, iron, cobalt, nickel, copper, silver, gold, zinc and cadmium. Suitable examples of the amine can be any selected from the group consisting of methylamine, methoxylamine, methylenediamine, bromoethylamine, chloroethylamine, fluoroethylamine, dimethylamine, ethylenediamine, diethylamine, cystamine, aniline, nitro-benzenediamine, phenylenediamine, tris(2-chloroethyl)amine, tromethamine, ethanolamine, diethanolamine and triethanolamine. Suitable examples of the quaternary ammonium can be any selected from the group consisting of tetramethylammonium, tetrabutylammonium, tetraethylammonium, triethylmethylammonium and tributylmethylammonium.

In one embodiment, the sucralfate-bile interaction is binding of bile acid, bile salt or conjugated bile acid or a combination thereof by sucralfate. Merely by way of example, the binding is in vitro equilibrium binding. In another example, the binding is in vitro kinetic binding. In yet another example, the binding is adsorption of bile acid, bile salt or conjugated bile acid or a combination thereof to sucralfate. Merely by way of example, the interaction or association delays the migration of bile acid, bile salt or conjugated bile acid or a combination thereof in the presence of sucralfate.

In one embodiment, the cell culture system comprises a tissue culture cell. In a further embodiment, the tissue culture cell comprises a mammalian cell. In an embodiment, the mammalian cell is selected from the group consisting of human cell, monkey cell, ape cell, mouse cell, rat cell, hamster cell, rabbit cell, guinea pig cell, cow cell, swine cell, dog cell, horse cell, cat cell, goat cell, and sheep cell. In a preferred embodiment, the mammalian cell is a human cell. In another embodiment, the mammalian cell is a mammalian epithelial cell. In a more preferred embodiment, the human cell is a human epithelial cell. In another embodiment, the mammalian epithelial cell is a mammalian intestinal epithelial cell. In a most preferred embodiment, the human epithelial cell is a human intestinal epithelial cell. In still a further embodiment, the human intestinal epithelial cell is Caco-2.

Suitable examples of NSAIDs includes any from the group consisting of aceclofenac, acetyl salicylic acid, choline magnesium salicylate, clonixin, diflunisal, magnesium salicylate, salicyclic acid, salicylate, salsalate, sodium salicylate, dexibuprofen, dexketoprofen, diclofenac, droxicam, etodolac, fenoprofen, flufenamic acid, flurbiprofen, indomethacin, isoxicam, ketoprofen, ketorolac, lomoxican, loxoprofen, meclofenamate, meclofenamic acid, mefenamic acid, meloxicam, naproxen, nabumetone, oxaprozin, phenylbutazone, piroxicam, sulindac, tenoxicam, tolfenamic acid, tolmetin, ibuprofen, Cox-2 inhibitors and tramadol. In one embodiment, the NSAID is indomethacin.

In one embodiment, the nonselective inhibitor of cyclooxygenase (COX) 1 and 2 is selected from the group consisting of aspirin, diclofenac, ibuprofen, naproxen, mefenamic acid, indomethacin, ketoprofen and piroxicam and equivalents thereof.

Suitable examples of cell damage include any from the group consisting of cell death, necrosis, apoptosis, gastric lesion, loss in mucosal barrier, loss in barrier property of intestinal epithelium, decrease in transmucosal electrical potential difference, and loss of cell monolayer's transepithelial electrical resistance (TEER). In one embodiment, cell damage comprises loss of cell monolayer's transepithelial electrical resistance (TEER). In another embodiment, cell damage is loss of cell monolayer's transepithelial electrical resistance (TEER).

In one embodiment, the values for quantifying the sucralfate-bile interaction and quantifying the cell damage for the sucralfate suspension sample are obtained from multiple measurements of a single lot of sucralfate suspension sample or measurements from multiple lots of sucralfate suspension sample or a combination thereof. In another embodiment, the values for the sucralfate suspension RLD to be used in comparing the sucralfate-bile interaction and comparing the cell damage are obtained from two or more lots of sucralfate suspension RLD. In yet another embodiment, the reference values for the sucralfate suspension RLD to be used in comparing the sucralfate-bile interaction and comparing the cell damage are experimentally determined values characterized by a minimum and a maximum value and in vitro bioequivalence includes no less than about 80% of the values for the sucralfate suspension sample to be within the range of reference values when comparing the sucralfate-bile interaction and the cell damage, respectively. In yet another embodiment, the reference values for the sucralfate suspension RLD to be used in comparing the sucralfate-bile interaction and comparing the cell damage are experimentally determined values characterized by a minimum and a maximum value and in vitro bioequivalence includes no less than about 90% of the values for the sucralfate suspension sample to be within the range of reference values when comparing the sucralfate-bile interaction and the cell damage, respectively.

In one embodiment, the reference values for the sucralfate suspension RLD in comparing sucralfate-bile interaction and comparing cell damage are experimentally determined values characterized by a minimum and a maximum value and in vitro bioequivalence requires substantially or nearly all of the values for the sucralfate suspension sample to be within the range of reference values in sucralfate-bile interaction and cell damage, respectively. In one example, the reference values for comparing the sucralfate-bile interaction for the sucralfate suspension RLD is the range of about 7 to about 17 mg/mL including e.g., 7.08 to about 16.14 mg/mL, wherein the reference values for the sucralfate suspension RLD are derived from a set of values obtained from quantifying the sucralfate-bile interaction for 2 or more lots of the sucralfate suspension RLD. In another example, the reference values for comparing the cell damage for the sucralfate suspension RLD is a TEER range of about 23 to about 75% including e.g., about 23.3% to about 74.8%, wherein the reference values of the sucralfate suspension RLD are derived from a set of values obtained from quantifying the cell damage for 2 or more lots of the sucralfate suspension RLD. In yet another example, the reference values for comparing the cell damage for the sucralfate suspension RLD has a TEER range of about 64% to about 93% including e.g., about 64.3% to about 92.5%. Measurements are conducted under well-controlled conditions so as to permit comparison of the measured results for sucralfate suspension RLD and sucralfate suspension sample.

In one embodiment, the values are statistical means. In a further embodiment, the means of the values determined for the sucralfate suspension sample fall within two standard deviations of the means determined for the set of reference values set for the sucralfate RLD. In another embodiment, the means of the values determined for the sucralfate suspension sample are within one standard deviations of the means determined for the set of reference values set for the sucralfate RLD.

In one embodiment, the sucralfate suspension sample is said to have in vitro bioequivalence to a sucralfate suspension RLD when (i) the value determined in quantifying the sucralfate-bile interaction of the sucralfate suspension sample with a bile acid, bile salt and/or conjugated bile acid or a combination thereof is within the range of the set of SCFeq values obtained from quantifying the sucralfate-bile interaction for 2 or more lots (including 3 or more; 4 or more; or 5 or more lots) of the sucralfate suspension RLD; (ii) the TEER values determined in quantifying the cell damage of the sucralfate suspension sample with a cell culture system is within the set of values obtained from quantifying the cell damage for 2 or more lots of the sucralfate suspension RLD; (iii) ratio of mean of the values (Mean of the Test/Mean of the RLD) determined in quantifying the sucralfate-bile interaction of the sucralfate suspension sample with a bile acid, bile salt and/or bile conjugate base or a combination thereof to the mean of the set of values obtained from quantifying the sucralfate-bile interaction for 2 or more lots (including 3 more; 4 or more; or 5 or more lots) of the sucralfate suspension reference listed drug; and (iv) ratio of mean of the values determined in quantifying the cell damage of the sucralfate suspension sample with a cell culture system to the mean of the set of values obtained from quantifying the cell damage for 2 or more lots of the sucralfate suspension reference listed drug is within the range of about 0.80 to 1.25; and (v) the about 90% confidence interval on the difference in product means falls entirely within the range from −EAC to +EAC; where EAC is the Equivalence Acceptance Criterion selected as EAC=1.5×S where S is the square root of the total variance for RLD The invention further provides a method for obtaining a sucralfate suspension sample that is a bioequivalent of a sucralfate suspension RLD by determining in vitro bioequivalence.

The invention further provides a method for reducing or alleviating the symptoms associated with an ulcer in a patient suffering from the ulcer comprising administering to the patient an effective amount of any of the sucralfate suspension samples thereby reducing or alleviating the symptoms associated with an ulcer in the patient.

Advantages of the Invention

Bioequivalence (BE) assessment is essential for generic drug development and availability of any interchangeable product. The requirements for a BE study vary greatly from product to product for various reasons. The underlying scientific basis for the BE assessment for the generic drug product is that it should be safe and as effective as the reference drug product.

For the majority of drug products, the requirements of a BE study are both ethical and scientifically appropriate in accurately deducing a product's therapeutic equivalence. In the case of Sucralfate oral suspension, as of today there is no guidance from the FDA for assessing BE for Sucralfate.

For Sucralfate, a site of action is local in the GI tract. The drug product dissolution and transit controls the presentation of drug to the site of action and the drug's plasma concentration is downstream from the site of action and irrelevant to the clinical effect. It also has very low systemic availability and is not detected in plasma. As such, plasma levels of Sucralfate cannot be used to establish bioequivalence of a Sucralfate Suspension sample to a Sucralfate Suspension RLD.

The current invention provides an advantage by providing a method for establishing therapeutic equivalence of a pharmaceutically equivalent Sucralfate Suspension sample against a Sucralfate Suspension RLD. It provides a more accurate, sensitive and reproducible method than previously proposed and subsequently withdrawn method based on clinical endpoint. Not only is the in vitro bioequivalence method of the invention based on biochemistry and bioassay more accurate, sensitive and reproducible but it is also ethical, expeditious, robust and cost effective than a method based on clinical endpoint.

The following examples are presented to illustrate the present invention and to assist one of ordinary skill in making and using the same. The examples are not intended in any way to otherwise limit the scope of the invention.

EXAMPLES

Example 1

Bile-Acid Binding Assessment Using Taurodeoxycholate (TDC):

Optimized assay conditions are as follows: The TDC concentration was 2.5 mM. The Sucralfate concentrations were at 0.5, 1, 2, 4, 8, 16, 32 and 50 mg/mL. TDC is incubated with different concentrations of Sucralfate at pH 1.5 and 37° C. for 60 minutes; following incubation, each sample is spun at 12,500×g for 30 min at room temperature to remove TDC bound to Sucralfate. Concentration of free TDC is determined by collecting the supernatant and analyzing the presence of TDC by LC-MS/MS detection analytical method.

Sucralfiate adsorption of bile acids and salts—agents in erosive mucosal injury and ulceration. The gastric mucosal barrier is considered to play an important role in protecting the gastric mucosa from the destructive effects of several luminal agents including $H^+$ ions diffusing from the lumen into the mucosa (back-diffusion). This barrier consists of mainly three components: an epithelial cell lining where the cells are bound by tight junctions that repel harsh fluids that may harm the lining, a mucus covering which protects the mucosa from auto-ingestion by pepsin and from erosion by acids and other caustic materials ingested, and bicarbonate ions which act to neutralize harsh acids [16]. The breakdown of this barrier has been associated with erosive mucosal injury and ulceration induced by factors such as stress and endogenous compounds including bile acids, which is one of the major components of bile (67%) along with phospholipids (22%), proteins (4.5%), cholesterol (4%) and bilirubin (0.3%) [17]. Bile salts are composed of the salts of four different kinds of free bile acids (cholic, deoxycholic, chenodeoxycholic and lithocholic acids) and each of these acids combines with glycine or taurine to form conjugated bile acids and salts. Bile acids are considered to be one of the important factors in the pathogenesis of ulcer disease, and the binding of bile acids to antacids has been considered to play an important role in the therapeutic action in the treatment of ulcer [11]. The exact mechanism by which the bile salts disrupt the gastric mucosal barrier is unknown, and a couple of potential mechanisms postulated are the mucosal uptake of bile salts and dissolution of mucosal lipids by the detergent action of intraluminal bile salt micelles [18]. In the presence of acid, Sucralfate releases aluminum, acquires a strong negative charge and binds electrostatically to any positively charged chemical groups in its environment, including proteins, peptides, and drugs. Adsorption of bile acids to Sucralfate along with several aluminum-containing antacids has been examined thoroughly and widely published (19, 27). Potent bile acid binding properties of Sucralfate, which are pH-dependent, have been reported [11]. Therefore, for all of the reasons stated above, it was deemed critical to compare the bile acid binding capacity of the RLD product with that of the test product to be able to compare the protective action of Sucralfate using both products.

Experiments were then executed as per the assay eligibility determination process below. The results of each step are discussed below.

Step 1: Assay Development
  1. Determination of analytical sensitivity for determination of TDC concentrations
  2. Bile acid selection
  3. Optimum pH condition selection for bile acid binding
  4. Evaluation of TDC binding to Sucralfate at varied TDC concentrations for selection of optimal concentration of TDC for comparative studies
  5. Incubation duration
  6. Sample preparation procedures Step 2: Assay Qualification
  1. Evaluate assay reproducibility
  2. Determine assay selectivity by evaluating the dose-response of Sucralfate binding to TDC
  3. Evaluate the range of Sucralfate binding to bile acids using multiple lots of RLD.

Step 3: Assay Performance
  1. Evaluate binding of TDC for the initial prototype test formulation (Test_50) and compare with that of the reference formulation(s)
  2. Evaluate binding of TDC for the further optimized test formulation (Test_66) and compare with that of the reference formulation(s)

Results and Discussion

Step 1: Assay Development:
1. Determination of Analytical Sensitivity for Determination of TDC Concentrations:

Multiple standard curves were generated to determine and confirm the analytical sensitivity for the detection of TDC using LC-MS/MS methodology for detection. The range of TDC concentrations evaluated was 0-40 µM. The results, as illustrated in FIG. 1, showed that the standard curves generated under these conditions were consistently reproducible and the assay was sufficiently sensitive to detect TDC.

2. Bile Acid Selection:

Several conjugated bile acids such as glycocholate (GC), glycochenodeoxycholate (GCDC), glycodeoxycholate (GDC), taurocholate (TC), taurodeoxycholate (TDC), and taurochenodeoxycholate (TCDC) among others, have been reported to be present in human gastric and duodenal aspirates [11]. Graham et al. (1984) reported that Sucralfate had the maximum binding capacity to TDC and TCDC (with binding capacity to TDC being greater as compared to TCDC). Therefore, both TDC and TCDC were selected for the in-vitro evaluation of bile acid binding properties of Sucralfate. TDC was then chosen as the bile acid for further assessments based on the findings that the binding capacity of Sucralfate was greater for TDC as compared to TCDC.

3. Optimum pH Condition Selection for Bile Acid Binding and Evaluation of TDC Binding to Sucralfate at Varied TDC Concentrations for Selection of Optimal Concentration of TDC for Comparative Studies:

Several aspects of the assay design such as assay pH, duration, TDC concentration, and sample preparation procedures were adapted from various references such as the Graham et al. and Lipsett et al. publications and findings were confirmed and/or further optimized [11,19]. Both pH- and concentration-dependent binding of Sucralfate to various bile acids has been reported, with much greater bile acid binding by Sucralfate at lower pH [11]. Additionally, concentrations used for various bile acid(s) in these studies varied from 1 to 10 mM, and concentrations for TDC specifically ranged from 1 to 5 mM.

Based on the abundant information available for assay conditions in the literature, 1) TDC binding to Sucralfate was evaluated at pH 1.5 and 4.5 and 2) TDC binding to Sucralfate was evaluated at 3 different TDC concentrations: 1, 2.5 and 5 mM for using Sucralfate concentration range of 2 to 50 mg/mL using an assay duration of 60 minutes.

Figure 2:
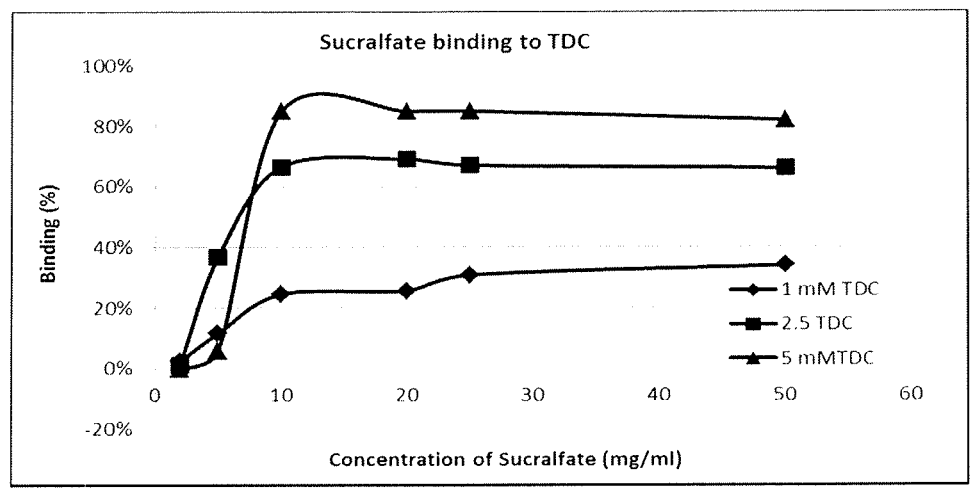
FIG. 2. Binding of TDC to Sucralfate at different concentrations of TDC.

Based on the results of the optimization experiments, the assay conditions were then fixed as outlined above. Each assay condition was chosen because it resulted in maximum binding of Sucralfate at that particular condition allowing it to be the most discriminatory condition for the purpose of comparing the RLD and test products. A concentration of 2.5 mM TDC was selected as it appeared to have the greatest dynamic range of % bound for the range of Sucralfate concentrations evaluated FIG. 2. An assay pH of 1.5 was selected based on several references that reported maximum Sucralfate binding to bile acids at lower pH which was also confirmed by results generated in house.

Step 2: Assay Qualification:

1. Evaluation of Assay Reproducibility:

Once the assay conditions were optimized, reproducible assay performance was confirmed by evaluating the Sucralfate binding to TDC in replicates using the optimized conditions using one lot of RLD product. The results confirmed the reproducibility of the assay using the fixed experimental conditions as tabulated in Table 1.

TABLE 1

Evaluation of assay reproducibility and dose-response of Sucralfate binding to TDC using one representative lot of RLD product (RLD_04)

| Sucralfate Concentration (mg/ml) | RLD_04 TDC binding | SD |
|---|---|---|
| 50 | 75% | 12% |
| 32 | 74% | 9% |
| 16 | 62% | 6% |
| 8 | 20% | 17% |
| 4 | 5% | 7% |
| 2 | 2% | 3% |

2. Determination of Assay Selectivity by Evaluating the Dose-Response of Sucralfate Binding to TDC:

Along with getting a sense of the reproducibility of the assay above, insights into the dose response relationship for Sucralfate binding to TDC was also achieved. The assay was performed using a fixed TDC concentration (2.5 mM) and pH (1.5) based on the results of the optimization experiments above and was evaluated for Sucralfate concentrations ranging from about 2 to 50 mg/mL using one lot of RLD product (RLD_04). The SCFeq (defined as the concentration of Sucralfate at half-maximal binding of TDC to Sucralfate at equilibrium) was determined to be about 16.14 mg/mL and the results indicated that the concentrations chosen for Sucralfate provided sufficient dynamic range for TDC binding to be able to delineate differences in binding between the test and RLD product in the assessments to follow. TDC binding was between about 2 and 75% for the chosen concentration range of Sucralfate for RLD_04 and about 18 to 85% for RLD_96. The results indicate that the assay has the ability to discriminate the binding of Sucralfate to TDC for Sucralfate concentrations of up to at least about 50 mg/mL.

Figure 3:
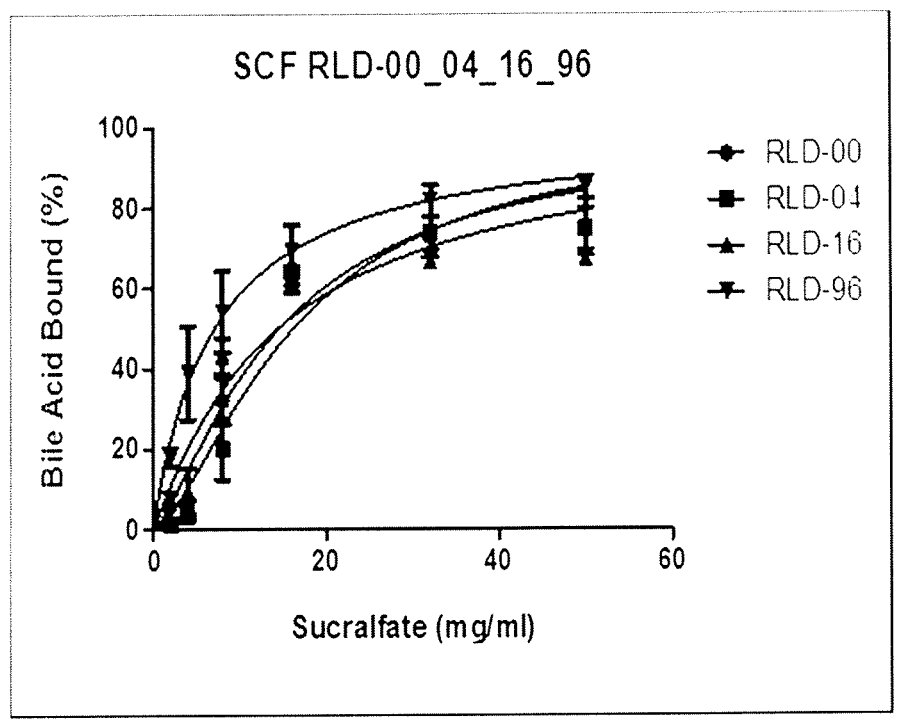
FIG. 3. Dose-response for Sucralfate binding to TDC using four lots of RLD product. Data represented as mean±SD.

3. Evaluation of the Range of Sucralfate Binding to Bile Acids Using Multiple Lots of RLD:

Once the dose-response of Sucralfate binding to TDC was observed using one lot of RLD product, assessments with additional available lots of RLD was commenced to determine the SCFeq value for each lot. The SCFeq value of each lot was calculated, which ranged between about 7.08 and 16.14 mg/mL for the four RLD lots (FIG. 3). These evaluations allow for the determination of the lot-to-lot variability of the RLD product, which can be used as the tolerance limits for comparative evaluation of test product performance.

The results provide sufficient confidence in the assay reproducibility and in the selectivity of the assay to detect differences in formulations compared to the RLD product. Furthermore, the range in % of TDC binding obtained from the evaluation for multiple lots of RLD provides insights into the variability of the RLD binding and can serve as limits of tolerance for the test formulations. The assay was deemed eligible and sufficiently qualified at this stage.

The table 2 below provides a range for the SCFeq value for each lot of RLD based on a 90% Confidence Interval:

| RLD Lot # | SCFeq | 90% CI |
|---|---|---|
| RLD_00 | 14.55 | 12.25 to 16.84 |
| RLD_04 | 16.14 | 13.79 to 18.48 |
| RLD_16 | 14.37 | 11.44 to 17.29 |
| RLD_96 | 7.08 | 5.34 to 8.82 |

RLD 00, RLD 04, RLD 16 and RLD 96 are different lots of Carafate suspensions purchased from Forest Labs.

TABLE 3

Qualitative (Q1) and Quantitative (Q2) comparison of RLD and Test products for Sucralfate oral suspension

| | | RLD(CARAFAT®) Lot #: RLD_45 Qty (g/100 mL) | Test formulations Lot #: Test_50 Qty (g/100 mL) | Test_66 Qty (g/100 mL) |
|---|---|---|---|---|
| Ingredient | Function | | | |
| Sucralfate | API | 10.00 | 10.00 | 10.00 |
| Microcrystalline Cellulose NF | Suspending Agent | 1.00* | 1.50 | 1.50 |
| Colloidal Silicon dioxide NF | Suspending Agent | 0.20* | 0.20 | 0.20 |
| Methyl Cellulose USP | Suspending Agent | 0.25* | 0.25 | 0.25 |
| Glycerin 99.5% USP | Bodying Agent | 9.90$ | 9.90 | 9.90 |
| Simethicone 30% Emulsion | Antifoaming Agent | 0.30* | 0.30 | 0.30 |
| Methyl Paraben | Preservative | 0.20* | 0.20 | 0.20 |
| Sorbitol 70% Solution USP | Bodying Agent | 27.0$ | 20.0 | 29.0 |
| Water DI Filt. | Vehicle | Q.S. | Q.S. to 100 mL | Q.S. to 100 mL |
| FD&C Red 40 | Colorant | Not listed in patents/ Literature | 0.66 | 0.657 |
| Cherry Maraschino Artificial Flavor #2359 | For Taste | Not listed in patents/ Literature | 0.10 | 0.10 |

Figure 4:
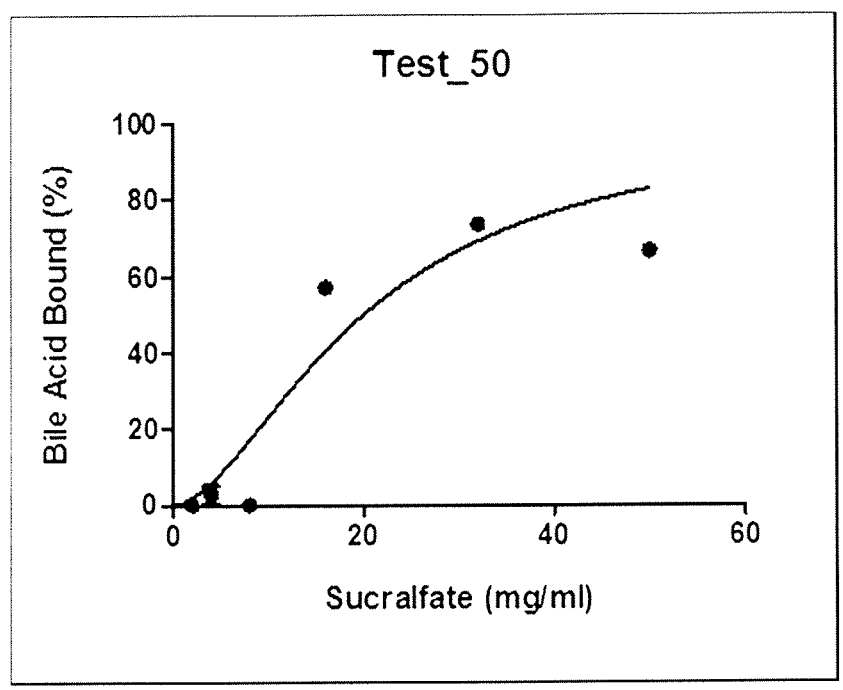
FIG. 4. Dose-response for TDC binding to Sucralfate using prototype Test formulation (Test_50).

Step 3: Assay Performance:

1. Evaluation of Binding of Sucralfate to TDC for the Initial Prototype Test Formulation (Test_50) and Comparison with that of the Reference Formulation(s):

Once the range of % binding and SCFeq values was determined using multiple RLD lots, the assay was performed using the early prototype test formulation (Test_50) using the same assay conditions (FIG. 4). The test formulation used here for comparison with the four RLD product lots is the initial prototype formulation that had undergone limited Q3 (microstructure; structural) characterization. In addition, the RLD characterization was also ongoing along with the determination of the CPPs (Critical Process Parameters) for the formulation manufacturing process. A SCFeq value of 20.06 mg/mL was obtained, higher than the SCFeq values obtained for the RLD product lots (7.08-16.14 mg/mL; RLD SCFeq Value range based on 90% CI interval: 5.34 to 18.48). This clearly demonstrates the ability of the assay to discriminate a "different" formulation and also corroborate the comparative findings of the physicochemical parameters evaluated to establish similarity in the formulation function. As the assay and the approach further develop, statistical analysis for establishing acceptance criteria for product similarity will be performed based on the factors evaluated in the assay validation stage. As this adds another bioassay measurement supportive of the postulated modes of action and the formulation CQAs (Critical Quality Attributes), the use of the in-vitro approach is further justified.

Figure 5:
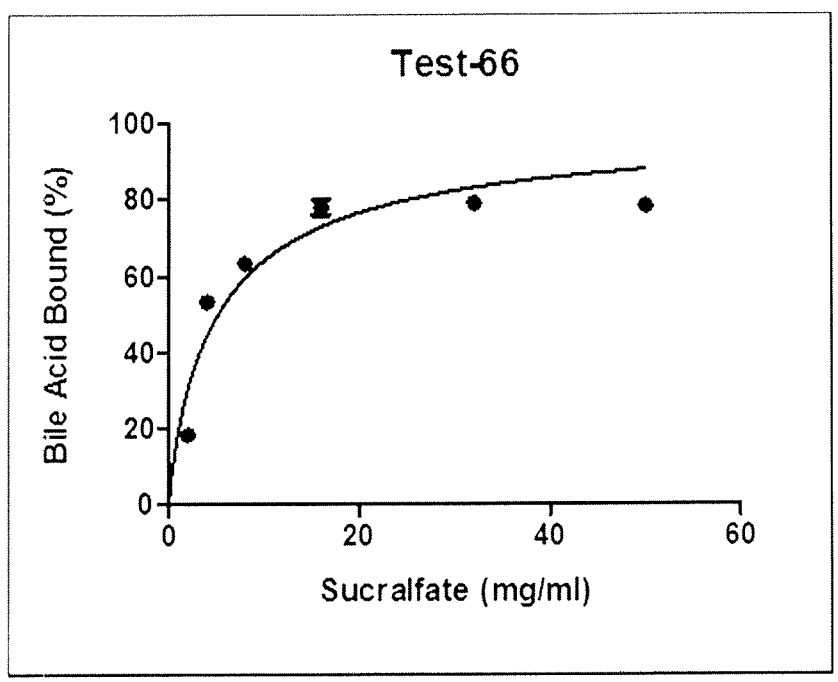
FIG. 5. Dose-response for TDC binding to Sucralfate using further optimized test formulation (Test_66).
Figure 6:
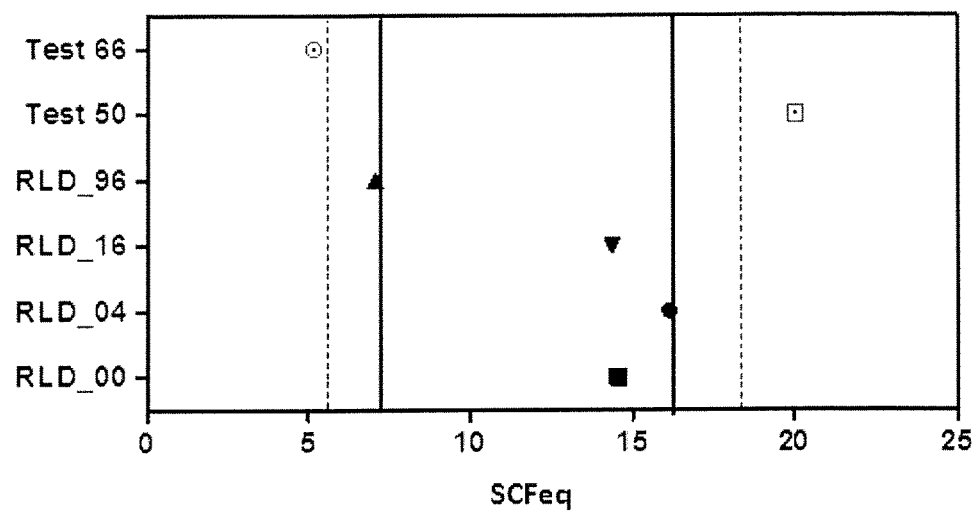
FIG. 6. Comparative performance assessment of the initial prototype test lot (Test_50) and further optimized test formulation (Test_66) for Sucralfate binding to TDC using the performance range criteria from four lots of RLD.

2. Evaluation of Binding of Sucralfate to TDC Using the Further Optimized Test Formulation (Test_66) and Comparison with that of the Reference Formulation(s):

As the formulation development efforts progressed, a further optimized test formulation (Test 66) was evaluated in for TDC binding to Sucralfate using the optimized assay conditions (FIG. 5). The SCFeq value obtained for Test_66 was 5.17 mg/mL, closer to the range of SCFeq values determined for the four RLD lots (7.08 to 16.14 mg/mL; RLD SCFeq value range based on 90% CI interval: 5.34 to 18.48) as compared to Test_50 (SCFeq=20.06 mg/mL) (FIG. 6). This demonstrates the ability of the assay to detect differences in the formulation composition (Q2 (quantitative) is different for Test_66 as compared to Test_50) and the manufacturing process between Test_66 and Test 50 products and will be used to guide further formulation development efforts.

Example 2

Cytoprotective Ability
Increase in the Potential Difference (Electrical Resistance) of Cells:

Optimized assay conditions are as follows: Indomethacin concentration was at 2 mM; pH for apical dosing solution was at 6.0. Sucralfate concentration was at 2.5 and 5 mg/mL. The assay duration was at 2 hours.

An ulcer develops as a result of an imbalance between aggressive factors and mucosal defensive mechanisms. The unstirred layer covering the mucosal luminal surface maintains a neutral microenvironment at the surface epithelial cells and is the first line of mucosal defense. The second line of mucosal defense is formed by a continuous monolayer of epithelial cells which secrete mucus and bicarbonate and generate prostaglandins. The plasma membrane lipid bilayer of the epithelial cells is hydrophobic, repelling acid- and water-soluble damaging agents. Interconnected by tights junctions, the mucosal epithelial cells form a barrier preventing back-diffusion of acid and pepsin.

Direct cellular damage due to necrotizing agents and the development of gastric lesions has been previously correlated with a decrease in the transmucosal electrical potential difference (PD) of the membrane barrier accompanied by net flux of $Na^+$, $Cl^-$, and $H^+$ ions across the gastrointestinal mucosa [24]. A human intestinal epithelial cell culture system (Caco-2) exhibits morphological, biochemical, and functional characteristics similar to those of human intestinal mucosa in vivo, such as the expression of cell polarity and tight junctions. Caco-2 cells have been extensively used to study the barrier properties of human intestinal epithelium with regard to drug transport, paracellular flux of hydrophilic solutes, and transcellular passive diffusion of lipophilic solutes among many other applications [24]. PD (measured as the cell monolayer's transepithelial electrical resistance (TEER)), a measure of the integrity of the cell monolayer and its barrier properties, has also been studied and reported previously in evaluating the damage caused by acid and the protective effect of Sucralfate on the gastric mucosal barrier [24]. For all of the above reasons, the Caco-2 cell monolayer model was selected for evaluating the cytoprotective activity of Sucralfate and experiments were executed as per the assay eligibility determination process below. The results of each step are discussed below.

Figure 7:
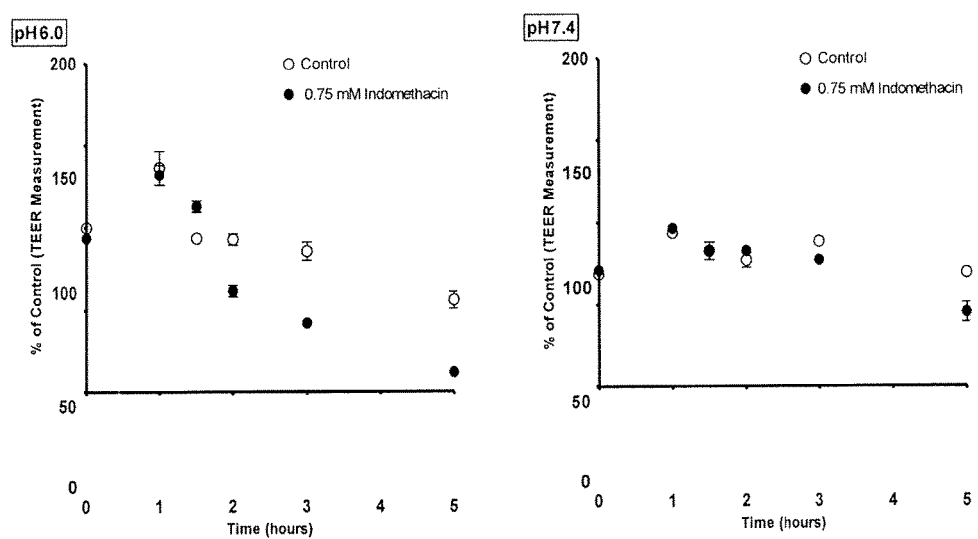
FIG. 7. Optimization of pH condition for cytoprotective assay. Comparison of TEER measurements between the control treatment and the indomethacin treatment at two different apical pH conditions (6.0 and 7.4). Results are presented as mean±SD.

Step 1: Assay Development
1. pH optimization
2. Indomethacin concentration optimization
3. Assay duration optimization Step 2: Assay Qualification:
1. Evaluate reproducibility
2. Evaluate assay selectivity by evaluating dose discriminating ability of the assay
3. Establish the range in % TEER remaining using multiple lots of RLD Step 3: Assay Performance:
1. Evaluate the cytoprotective ability of Sucralfate using the initial prototype formulation (Test_50) and compare with the RLD product lot
2. Evaluate the cytoprotective ability of Sucralfate using the further optimized test formulation (Test_66) and compare with the RLD product lot Results and Discussion Step 1: Assay Development:
1. Evaluation of Optimal pH Condition:

Considering the fact that the Caco-2 cell model mimics the human intestinal mucosa, and that the intraluminal pH of the small intestine ranges from approximately 6.0 to 7.4, evaluation of the damage induced by indomethacin (the chosen ulcerogenic agent, the use of which was previously reported [24]) was performed at these two pH conditions. The choice of 0.75 mM indomethacin was based on earlier observations reported for a similar evaluation using Caco-2 cells for this initial assay development stage [24]. For each pH condition, the damage was measured by comparing the TEER values of indomethacin-treated cell monolayers with those of control cell monolayers before and after the assay, and the % of TEER remaining (compared to the control treatment) was calculated. The results are illustrated below in FIG. 7. The results indicate that despite the long duration, at pH 7.4, a significant loss of TEER was not observed in the treatment with indomethacin. In contrast, for the assay with the pH condition of 6.0, approximately 50% of the TEER was lost by two hours and nearly 80% of the TEER was lost by the end of the assay duration of 5 hours. To demonstrate Sucralfate's ability to protect the cells from damage from necrotizing agents, it is desirable to induce sufficient damage to provide adequate dynamic range to demonstrate the cytoprotective ability of Sucralfate with sufficient sensitivity to discriminate between various formulations. Therefore, pH 6.0 was selected as the optimal pH condition on the apical (modeling the luminal) side for this assay. It was also noted that the majority of the damage was caused between 2 and 3 hours of duration; any additional damage after three hours was marginal. For this reason, further evaluations were performed at a truncated duration of 2 to 3 hours. See FIG. 7.

Figure 8:
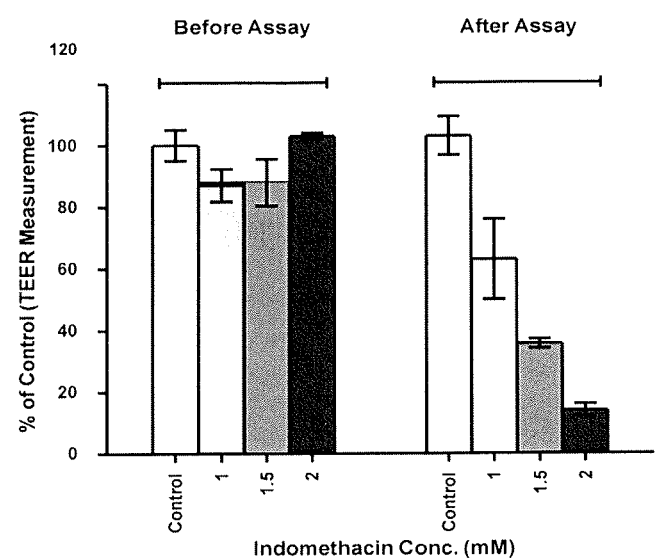
FIG. 8. Dose-response of Indomethacin. Results are presented as mean±SD.

2. Optimization of Indomethacin Concentration:

Considering the fact that significant damage to the cells was induced post two hours in the assessment above and the fact that a shorter assay duration would be desirable for the purposes of experimental logistics, different concentrations (1, 1.5 and 2 mM) of indomethacin were tested to understand the extent of damage caused to the cell monolayers as a function of indomethacin concentration using apical pH of 6.0 and a 3 hour duration. Maximum damage was observed at 2 mM indomethacin as illustrated in FIG. 8. Therefore, a concentration of 2 mM was selected as the optimal concentration for this assay.

Figure 9:
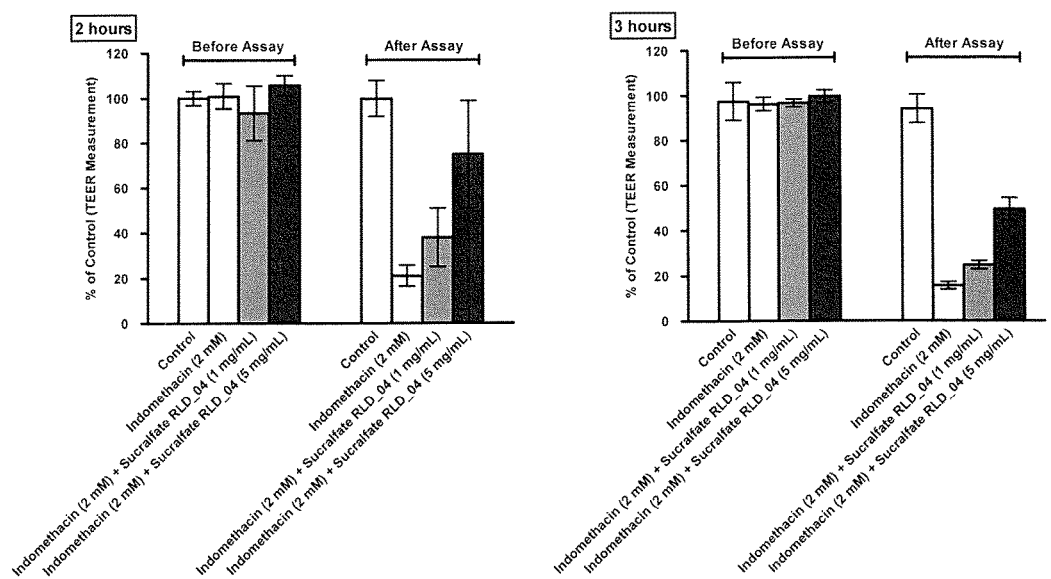
FIG. 9. Assay duration optimization evaluation. Results are presented as mean±SD.

3. Optimization of Assay Duration:

Additional assessments were performed to ensure that sufficient damage was elicited by indomethacin at 2 mM using a 2-hour assay duration with and without Sucralfate at two different concentrations. The results as illustrated in FIG. 9, indicated that both the durations (2 and 3 hours) elicited sufficient damage, however, it appeared that the recovery of TEER for both concentrations of Sucralfate (1 and 5 mg/mL) was higher for the 2 hour assay duration as compared to the 3 hour assay duration. Therefore, 2 hours was chosen as the assay duration for further evaluations.

Based on these assessments, the above-listed assay conditions were chosen to qualify the assay by evaluating the assay reproducibility and the dose-dependent cytoprotective ability of Sucralfate.

Figure 10:
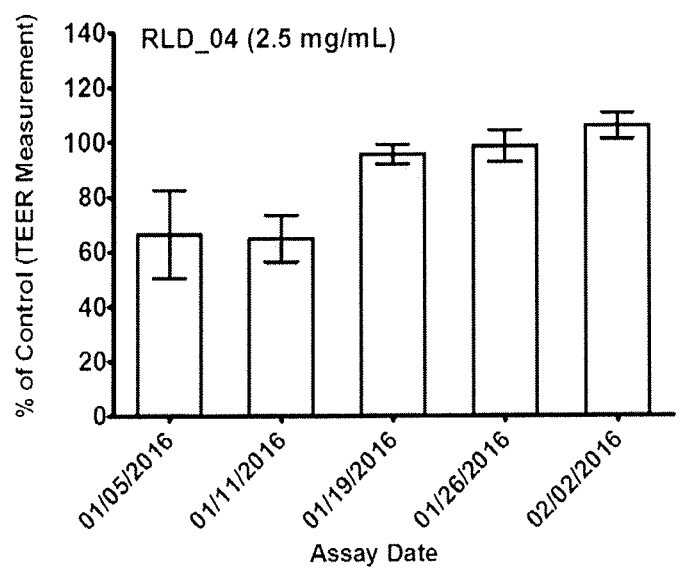
FIG. 10. Evaluation of assay reproducibility using one lot of RLD product using Sucralfate concentration of 2.5 mg/mL. Results are presented as mean±SD.
Figure 11:
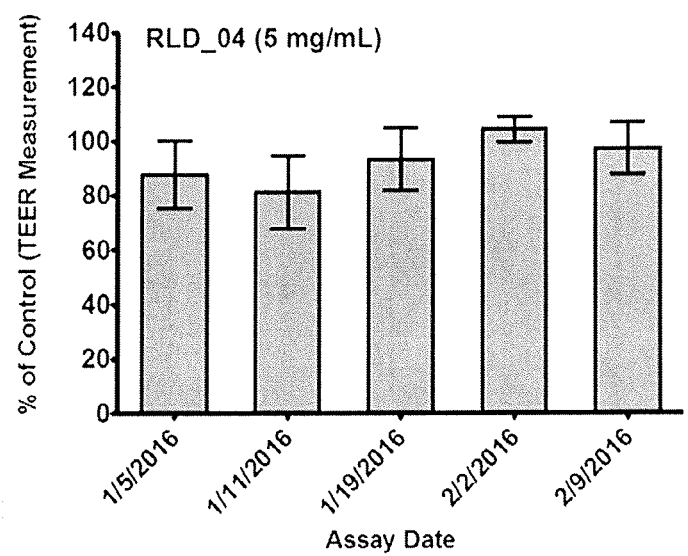
FIG. 11. Evaluation of assay reproducibility using one lot of RLD product using Sucralfate concentration of 5.0 mg/mL. Results are presented as mean±SD.

Step 2: Assay Qualification:

1. Evaluation of Assay Reproducibility:

The reproducibility of the assay was evaluated by repeating the assay multiple times and calculating the % of TEER remaining after incubation with two concentrations of Sucralfate (2.5 and 5 mg/mL) using one lot of RLD product (RLD_04), as illustrated in FIGS. 10 and 11. It was observed that the assay was reproducible and the % TEER remaining (as compared to the control treatment) after 2 hours for the treatment co-dosed with Sucralfate ranged between about 81-104% for the 5 mg/mL treatment and about 65 to 106% for the 2.5 mg/mL treatment. Further assessments were then commenced to evaluate the assay selectivity.

Figure 12:
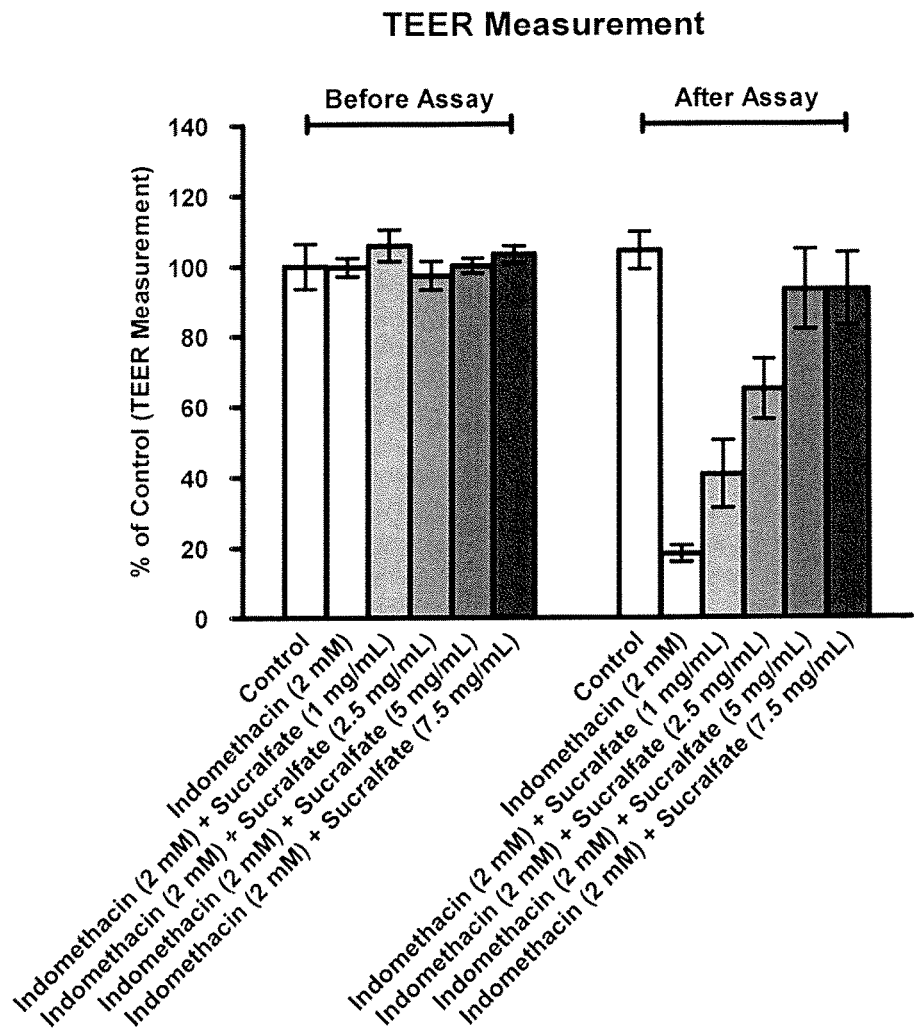
FIG. 12. Dose response of Sucralfate using one lot of RLD product (RLD 04). Data presented as mean±SD.

2. Evaluation of the Assay Selectivity by Evaluating its Dose-Discriminating Ability:

Once the assay reproducibility was confirmed, further assessments were made to evaluate the dose-response of Sucralfate using multiple concentrations of Sucralfate RLD product lot (RLD_04). FIG. 12 below illustrates the results. An increase in cytoprotectiveness, as measured by the % of TEER remaining when compared to the control treatment, was seen with increasing Sucralfate concentrations up to 5 mg/mL. At 7.5 mg/mL, no additional increase in % TEER remaining was observed as compared to the 5 mg/mL treatment. The assay's dose-discriminating ability is evident only up to 5 mg/mL; therefore, further assessments will be performed at concentrations of 5 mg/mL or less.

Figure 13:
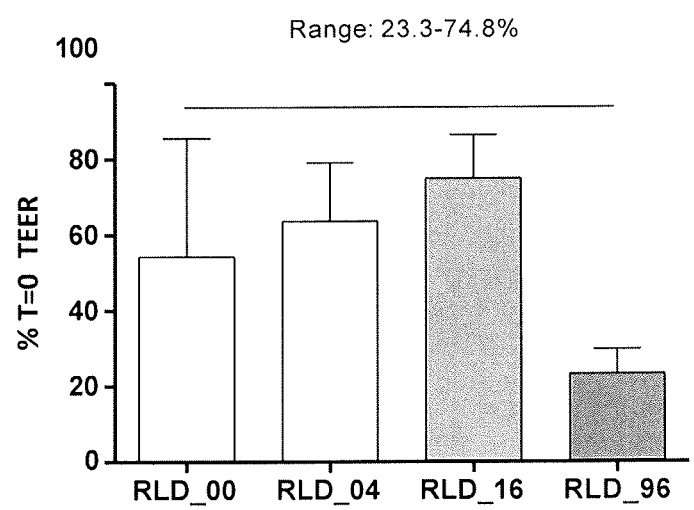
FIG. 13. Evaluation of inter-lot variability in cytoprotective ability using four lots of RLD product at 2.5 mg/mL Sucralfate concentration. Results presented as mean±SD.
Figure 14:
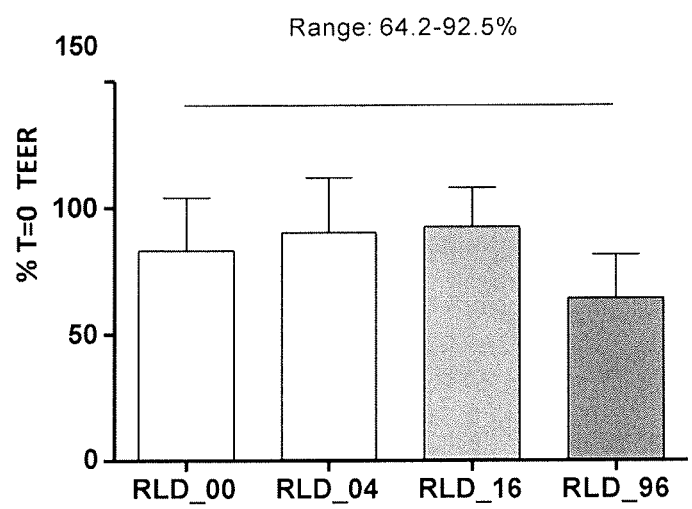
FIG. 14. Evaluation of inter-lot variability in cytoprotective ability using four lots of RLD product at 5.0 mg/mL Sucralfate concentration. Results presented as mean±SD.

3. Establishing the Range of % TEER Remaining Using Multiple Lots of RLD:

Four lots of RLD product were then evaluated for cytoprotective ability to evaluate the range of % TEER remaining using two concentrations of Sucralfate (2.5 and 5.0 mg/mL). This would allow the establishment of tolerance limits for comparison with the Test product lots. For the 2.5 mg/mL concentration, the range for % of TEER remaining for all four lots of RLD product was observed to be 23.3 to 74.8% as illustrated in FIG. 13 and for the 5.0 mg/mL concentration, the range of % TEER remaining for all four lots of RLD product was observed to be 64.2 to 92.5% as illustrated in FIG. 14.

Figure 15:
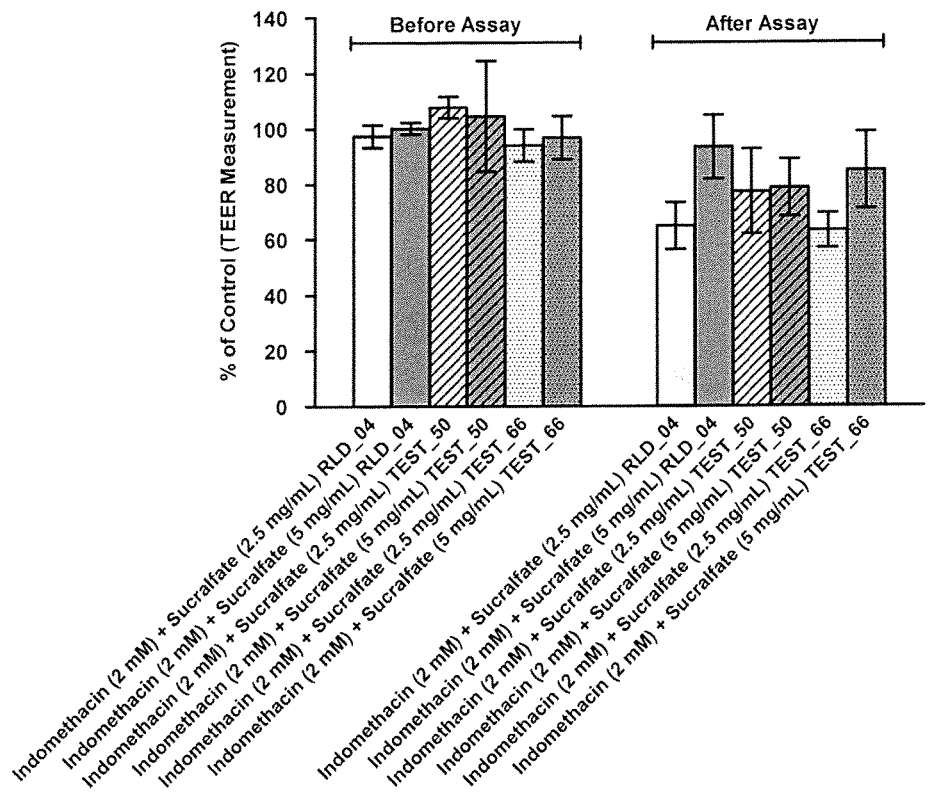
FIG. 15. Comparison of cytoprotective ability between the test and RLD products. Results are presented as mean±SD.

Step 3: Assay Performance:

1. Evaluation of the Cytoprotective Ability of Sucralfate for the Initial Prototype Formulation (Test_50) and Further Optimized Formulation (Test_66) and Comparison with the RLD Product Lots:

The initial prototype test formulation lot (Test_50) and the further optimized test formulation lot (Test_66) were then evaluated and compared with a RLD product lot (RLD_04) using two concentrations of Sucralfate (2.5 and 5 mg/mL). The results exhibited cytoprotective effects for both RLD and test product lots as illustrated in FIG. 15 for both concentrations tested. For the RLD product lot (RLD_04), the % TEER remaining at the 2.5 mg/mL concentration was found to be about 63.6% and the % TEER remaining for the 5 mg/mL concentration was found to be about 90.3%. For the initial prototype formulation (Test_50), using the 2.5 mg/mL treatment, the % TEER remaining was about 77.3%, which was not within the range of RLD performance in this assay for this concentration (23.3% to 74.8%). Moreover, a dose-response was not observed for this Test lot (Test 50) and both the 2.5 and 5.0 mg/mL treatment groups had a similar % TEER remaining (2.5 mg/mL: 77.3% and 5.0 mg/mL: 78.8%) after the two hour incubation duration. For the more optimized test formulation (Test_66), the % TEER remaining for the 2.5 mg/mL treatment was 63.3%, which was within the RLD range of performance and a dose-response was observed for the two concentrations of Sucralfate (2.5 mg/mL: 63.3% and 5.0 mg/mL: 85.0%), similar to that observed for the RLD lot (RLD 04).

These findings again confirm the reproducible and selective nature of the assay. In addition, it demonstrates the ability of the assay to distinguish between formulations that are different as compared to the RLD product by clearly demonstrating a lack of dose-response for the Test_50 formulation, a formulation that was prepared in the very early stages of formulation development without having completed the reverse engineering and characterization of the RLD. Test_66 was prepared subsequently, after the reverse engineering of the RLD was completed along with the physicochemical characterization of the RLD and delineation of some of the CPPs (Critical Process Parameters). The results for the % TEER remaining for Test_66 not only demonstrated the expected dose-dependent response, but they were also "similar" to that of the RLD lot. This also indicates that this assay along with the remaining proposed assays can be used during the formulation optimization stages to prepare a final formulation that is not only close to the RLD in terms of function (as identified by the physicochemical characterization), but also close to the RLD in terms of the outcomes of the biological assays based on the postulated modes of action.

In summary, the Caco-2 cell monolayer model is a well-established, widely used, and accepted model that can be used as a tool to evaluate one of the key mechanisms of action of Sucralfate. The model is also discriminatory of formulation differences and can be used for formulation optimization followed by pivotal equivalence assessments.

Figure 16:
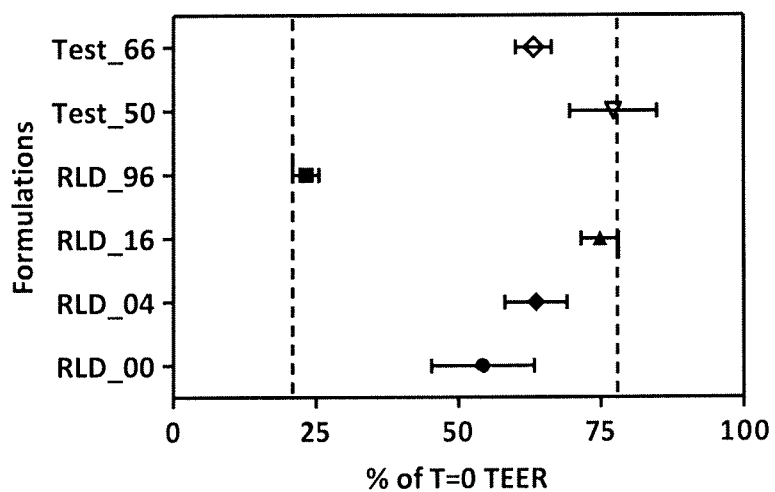
FIG. 16. Comparative performance assessment of the initial prototype test lot (Test_50) and the further optimized test lot (Test_66) using the performance range criteria from four lots of RLD at 2.5 mg/mL concentration.
Figure 17:
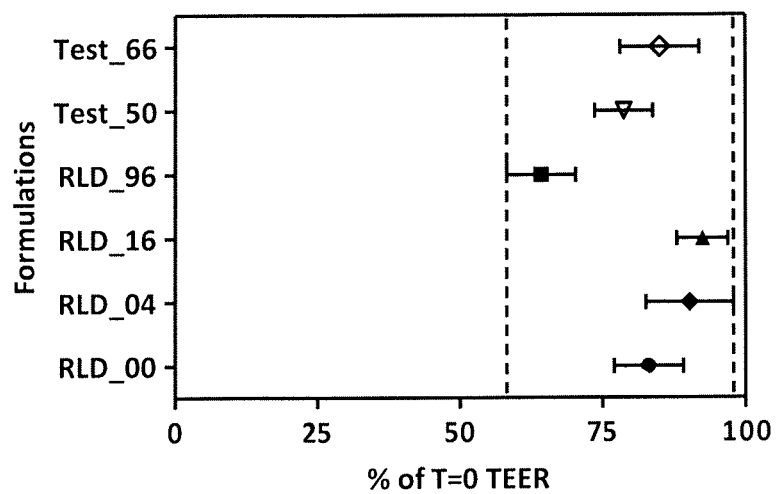
FIG. 17. Comparative performance assessment of the initial prototype test lot (Test_50) and the further optimized test lot (Test_66) using the performance range criteria from four lots of RLD at 5.0 mg/mL concentration.

The results from this study can build sufficient weight of evidence to demonstrate similarity RLD and test product and to establish therapeutic equivalence between the test product and the RLD product. See FIGS. 16-17.

Discussion

BE (bioequivalence) assessment is essential for approval of generic drug products. The requirements for a BE study vary greatly from product to product for various reasons. For some products, such as Sucralfate oral suspension, these requirements can be a huge barrier to market entry for generic products despite the need for the product and a lack of availability of any interchangeable product. The underlying scientific basis for the BE assessment for the generic drug product is that it should be safe and as effective as the reference drug product.

For the majority of drug products, the requirements of a BE study are both ethical and scientifically appropriate in accurately deducing a product's therapeutic equivalence. In the case of Sucralfate oral suspension, as of today there is no guidance from the FDA for assessing BE for Sucralfate. The draft guidance on Sucralfate, which was published in July 2014 by the FDA, required a three-arm, placebo-controlled, in-vivo clinical endpoint study in healthy males and females with dyspepsia symptoms and active duodenal ulcer disease, verified at screening endoscopy. Additionally, the enrolled patients had to be *H. pylori* negative or continue to have the presence of an ulcer after appropriate treatment and eradication of *H. pylori*. Furthermore, the duration of this study was 8 weeks, and not only is it challenging to recruit subjects for the study but it is also unethical to administer a placebo treatment to patients and allow for their continued suffering. The FDA acknowledged the challenge of this BE study requirement and encouraged sponsors to submit proposals for in vitro studies or any other methods for evaluating BE for this drug product in the 2014 Guidance.

For Sucralfate, the site of action is local in the GI tract. The drug product dissolution and transit controls the presentation of drug to the site of action and the drug's plasma concentration is downstream from the site of action and irrelevant to the clinical effect. It also has very low systemic availability and is not detected in plasma. For other drugs that are absorbed sparingly or not at all and intended for local activity, such as cholestyramine and sevelamer, in-vitro binding studies have been recommended by the US FDA to demonstrate BE and are deemed sufficient based on the mechanism of action of these drugs.

The mechanism of action of Sucralfate is non-systemic and, in general, Sucralfate exerts its effects by protecting the gastric mucosa against various irritants and providing a cytoprotective effect by enhancing natural mucosal defense mechanisms. Because various mechanisms of action have been postulated for Sucralfate, in-vitro binding studies, although critical in establishing BE, are not by themselves sufficient for establishing BE. For this reason, the proposed approach takes into consideration the interaction of Sucralfate throughout the upper GI tract where the drug product is presented, and the CQAs (Critical Quality Attributes) that determine formulation function are evaluated in conjunction with bioassays that support the postulated modes of action.

The approach includes similarity-by-design and begins with the development of a test product formulation which is qualitatively and quantitatively the same as the RLD with respect to the active and inactive ingredients. Based on the target product profile, the CQAs that affect the formulation function and biological effects have been identified and the critical material attributes and process parameters will be optimized until similarity of the test product in formulation function and in the bioassays with the RLD product is achieved. Once a similar prototype formulation is identified, scale-up batches will be prepared and evaluated for similarity using all assays that can be validated appropriately in preparation for an ANDA submission.

The purpose of the data generated thus far is to demonstrate the utility of each assay individually in evaluating the corresponding CQA that contributes to product efficacy and to demonstrate the use of equivalence agreement between orthogonal measurements to ensure and establish therapeutic equivalence. A clinical endpoint study has been acknowledged by the FDA and the scientific community to be the least accurate way to establish BE, and the use of multiple validated assays such as the ones described above can be a more accurate way to establish BE. An in-vitro based bioequivalence approach is accepted for several complex drug products such as acyclovir ointment, cyclosporine ophthalmic emulsion and tobradex ophthalmic emulsions based on sound scientific principles.

The formulation development scientists initiated several activities in parallel, including API (Active Pharmaceutical Ingredient) sourcing and evaluation, reverse engineering of the RLD formulation, review of chemistry, preparation of the target product profile, identification of the CMAs (Critical Material Attributes) and CPPs (Critical Process Parameters) that affect the CQAs (Critical Quality Attributes), equipment and methodologies required for various assessments, etc. Various R&D scale batches were prepared in the process and data was generated for selective parameters for each batch. Analytical techniques are well established for physicochemical/Q3 (microstructure/structural) characterization of oral suspensions with some techniques requiring equipment that is readily available at the in-house facility.

As the R&D batches were still being prepared and further optimized, an early lot of the test formulation prototype (Test_50) was selected for evaluations in biological assays to understand and discern any differences in formulation performance that can be identified in these assays when compared to the RLD lots. For all of the biological assays performed for Test_50 it was evident that it was "different" as compared to the multiple lots of RLD.

Focusing on the binding assessments, the SCFeq for the bile acid binding was comparatively higher for Test_50 as compared to the RLD lots (about 20.06 vs. about 7.08-16.14 mg/mL; RLD SCFeq value range based on about 90% CI interval: about 5.34 to 18.48), which suggests stronger binding/affinity of Sucralfate from the RLD formulation as compared to the test formulation. It is to be noted that Sucralfate binding in general is highest at low pH conditions; however, due to the pKa of the bile acids, at lower pH the non-ionized form of the bile acid conjugates predominate and tend to precipitate. Regardless, similarity must be demonstrated in the bile acid binding of Sucralfate and the assay clearly has the ability to discriminate between different formulations.

For the cytoprotective assay using Caco-2 cell monolayers, the % TEER remaining with Test_50 was lower compared to the % TEER remained for the RLD lots (Test_50: 78.8% vs. RLD range: 82 to 85%), which indicated somewhat less recovery of cells from the damage induced by indomethacin as compared to the recovery seen using the RLD lots. These initial assessments demonstrate that the initial prototype formulation (Test_50) is "different" compared to the RLD lots, as one would expect considering that various aspects of formulation design were not optimized including the Q2 (quantitative) and the CPPs (Critical Process Parameters).

Similarly, although the results for Test_66 also indicate that it is a "different" formulation, the optimization efforts commenced by the formulation development team are evident in the results.

With regard to bile acid binding, the SCFeq value for Test_66 (about 5.17) was much closer to the RLD range (about 7.08 to 16.14; RLD SCFeq Value range based on about 90% CI interval: about 5.34 to 18.48) as compared to the Test_50 (about 20.06) formulation. As mentioned previously, the Q2 of Test_66 is different as compared to Test_50, along with differences in process parameters such as homogenization time and order of addition of simethicone. These optimization efforts have clearly resulted in a formulation closer to the RLD and the bioassay is able to distinguish the known formulation differences between the Test 50 and Test 66 formulations.

For the cytoprotective assay, Test_66 is closer to the RLD, with the % TEER remaining being 85% (vs. 64.2-92.5% remaining for RLD lots) at 5 mg/mL, whereas only 78.8% of the TEER is remaining for the Test_50 formulation treatment. In addition, a dose-response was not observed using the Test_50 formulation, which is expected based on all optimization and qualification evaluations with the RLD. The dose-response is observed with Test_66, as expected. This further reinforces the positive direction of the formulation optimization efforts and demonstrates that these assays can be valuable tools throughout formulation development and for establishing BE.

REFERENCES

1. Carafate Suspension Product PIL.
2. McCullough, R. W., IBS, NERD and functional dyspepsia are immuno-neuronal disorders of mucosal cytokine imbalances clinically reversible with high potency Sucralfate. Medical hypotheses, March 2013, Volume 80, Issue 3, Pages 230-233.
3. FDA response to Consultation Re: Biocraft Sucralfate Tablet Submission on Apr. 27, 1988.
4. Draft Guidance on Sucralfate. Recommended July 2014, FDA.
5. http://www.fda.gov/ohrms/dockets/ac/05/briefing/2005-137B1_07_Nomenclature.pdf.
6. Code of Federal regulations. Title 21, Volume 5; CITE: 21CFR320.24.
7. The Merck Index. 10th ed. Rahway, N.J.: Merck Co., Inc., 1983., p. 1273.
8. http://intranet.tdmu.edu.te.ua/data/kafedra/internal/pharmakologia/classes_stud/en/nurse/and/ptn/Pharmacology/2r/15%20Drugs %20Affecting %20Gastrointesti nal %20System %20and %20Nutrition.html.
9. http://omedicine.info/en/Sucralfate.html.
10. http://www.ncbi.nlm.nih.gov/pubmed/8370300.
11. F. Halter, Daniel Hollander M. D., Guido N. J., Tytgat M. D. Sucralfate From Basic Science to the Bedside.
12. Patent on Sucralfate suspension. (http://www.google.co.in/patents/U.S. Pat. No. 5,563,258).
13. Cutting, K. F., Wound exudate: composition and functions. British Journal of community nursing. February 2003. Pages 4-9.
14. Ito, Y., Onada, Y., Nakamura, S. Tagawa, K., Fukushima, T., Suguwara, Y., and Takaiti, O. Effects of new anti-ulcer drug ecabet sodium (TA-2711) on pepsin activity. II. Interaction with substrate protein, Japan J. Pharmacol., 62, 175-181; 1999
15. Kawakami, K., Yasuda, M., Ishii, K., Kokusenya, Y., and Sato, T. A kinetic study of protein binding to ecabet sodium using quartz-crustal microbalance Chem. Pharm. Bull. 47(7)919-922; 1999.
16. Methods Find Exp Clin Pharmacol. 1989; 11 Suppl 1:19-25. The gastric mucosal barrier. Clamp JR1, Ene D.
17. Reshetnyak, V. Physiological and molecular biochemical mechanisms of bile formation. World J. of gastroenterol. 2013 Nov. 14; 19 (42): 7341-7360.
18. Duane, W. and Wiegand, D. Mechanism by which bile salt disrupts the gastric mucosal barrier in the dog. The Journal of clinical investigation, Volume 66, November 1980 1044-1049.
19. Graham, D. Y., Sackman, J. W., Giesing, D. H., and Runser, D. J. In Vitro Adsorption of Bile Salts and Aspirin to Sucralfate. Digestive diseases and sciences, Vol. 29, No. 5 (May 1984), pp. 402-406.
20. Furukawa, O., Matsui, H., & Suzuki, N. (1997). Effects of Sucralfate and its components on acid- and pepsin-induced damage to rat gastric epithelial cells. Japanese Journal of Pharmacology, 75: 21-25.
21. Sigma-Aldrich (n.d.). Technical bulletin for Protease Colorimetric Detection Kit (Product Code PC0100). Retrieved from http://www.sigmaaldrich.com/content/dam/sigma-aldrich/docs/Sigma/Bulletin/pc0100bul.pdf.
22. Okabe, S., and Amagase, K. An overview of acetic acid ulcer models—The history and state of the art of peptic ulcer research. Biol. Pharm. Bull. 28(8) 1321-1341.2005.
23. Dobrozsi, D. J., Smith, R. L., Sakr, A. A. Comparative mucoretention of Sucralfate suspensions in an everted rat esophagus model. International Journal of Pharmaceutics 189. 81-89. 1999.
24. Tang, A. S., Chikhale, P. J., Shah, P., Borchardt, R., Utilization of a human intestinal epithelial cell culture system (Caco-2) for evaluating cytoprotective agents.
25. Waiver of In vivo Bioavailability and bioequivalence studies for Immediate-release solid oral dosage forms based on a biopharmaceutics classification system. Guidance for industry. May 2015, FDA.
26. FDA definition of a suspension: https://www.fda.gov/ohrms/dockets/ac/06/briefing/2006-4241B1-02-30-FDA-Topical %20Dosage %20Forms %20Definitions %20Old %20%20.pdf.
27. SCF binding to free bile acids: https://www.ncbi.nlm.nih.gov/pubmed/2682004.

What is claimed is:

1. A method for determining in vitro bioequivalence of a sucralfate suspension sample to a sucralfate suspension RLD comprising:
   a. contacting the sucralfate suspension sample with a bile acid, bile salt and/or a conjugated bile acid or a combination thereof, so as to permit sucralfate-bile interaction, quantifying the interaction so as to obtain quantified values of the interaction and comparing said values to reference values for the sucralfate suspension RLD; and
   b. contacting the sucralfate suspension sample with a cell culture system in the presence of a Non-Steroidal Anti-Inflammatory Drug (NSAID) or a nonselective inhibitor of cyclooxygenase (COX) 1 and 2 so as to inhibit cell damage induced by the NSAID or nonselective inhibitor of COX 1 and 2 in the cell culture system, quantifying the cell damage so as to obtain quantified value(s) for the sucralfate suspension sample and comparing the said value(s) to reference values for the sucralfate suspension RLD, wherein the cell culture system comprises a monolayer of mammalian epithelial cells and the cell damage comprises loss of the cell monolayer's transepithelial electrical resistance (TEER);

wherein the reference values for the sucralfate suspension RLD in step (a) are derived from a set of values obtained from quantifying the sucralfate-bile interaction for 2 or more lots of the sucralfate suspension RLD; wherein sucralfate-bile interaction is interaction between sucralfate and bile acid, bile salt and/or conjugated bile acid or a combination thereof; and wherein the sucralfate suspension sample is to have said in vitro bioequivalence to a sucralfate suspension RLD when the values determined in (a) and (b) for the sucralfate suspension sample are within the reference values in (a) and (b) for the sucralfate suspension RLD, respectively.

2. The method of claim 1, wherein the bile acid is selected from the group consisting of allocholic acid (3 alpha, 7alpha, 12alpha-trihydroxy-5 alpha-cholanoic acid; CAS: 2464-18-8), 5alpha-deoxycholic acid (3alpha, 12alpha-dihydroxy-5alpha-cholan-24-oic acid), bitocholic acid, chenodeoxycholic acid (3 alpha,7alpha-dihydroxy-5beta-cholan-24-oic acid; CAS: 474-25-9), cholic acid (3alpha,7alpha,12alpha-trihydroxy-5beta-cholan-24-oic acid; CAS: 81-25-4), deoxycholic acid (3alpha,12alpha-dihydroxy-5beta-cholanic acid; CAS: 83-44-3), glycochenodeoxycholic acid (2-[[(4R)-4-[(3R,5 S,7R,8R,9 S, 10S,13R,14 S,17R)-3,7-dihydroxy-10,13-dimethyl-2,3,4,5,6,7,8,9,11,12,14,15,16, 17-tetradecahydro-1H-cyclopenta[a]phenanthren-17-yl]

pentanoyl]amino]acetic acid; CAS No.: 640-79-9), glycocholic acid (3 alpha,7alpha, 12alpha-trihydroxy-5beta-cholan-24-oylglycine; CAS: 475-31-0), hyocholic acid (3alpha,6alpha,7alpha-trihydroxy-5beta-cholan-24-oic acid; CAS: 547-75-1), hyodeoxycholic acid (3α,6α-Dihydroxy-5β-cholan-24-oic acid; CAS: 83-49-8), isochenodeoxycholic acid (3beta,7alpha-dihydroxy-5beta-cholanic acid; CAS: 566-24-5), 3beta,12alpha-Dihydroxy-5beta-cholanoic acid (CAS: 570-63-8), isolithocholic acid (3beta-Hydroxy-5beta-cholan-24-oic acid; CAS: 1534-35-6), isoursodeoxycholic acid (3beta,7beta-dihydroxy-5beta-cholan-24-oic acid; CAS: 78919-26-3), 12-epideoxycholic acid, lithocholic acid (3alpha-hydroxy-5beta-cholanic acid; CAS: 434-13-9), alpha-muricholic acid (3alpha,6beta,7alpha-trihydroxy-5beta-cholan-24-oic acid; CAS: 2393-58-0), beta-muricholic acid (3 alpha, 6beta, 7beta-trihydroxy-5beta-cholan-24-oic acid; CAS: 2393-59-1), omega-muricholic acid, murideoxycholic acid (3alpha,6beta-dihydroxy-5beta-cholanic acid), beta-phocaecholic acid (CAS: 105369-89-9), taurochenodeoxycholic acid (2-[[(4R)-4-[(3R,5 S,7R,8R,9S, 10S,13R,14S,17R)-3,7-dihydroxy-10,13-dimethyl-2,3,4,5, 6,7,8,9,11,12,14,15,16,17-tetradecahydro-1H-cyclopenta[a]phenanthren-17-yl]pentanoyl]amino]ethanesulfonic acid; CAS No.: 516-35-8), taurocholic acid (2-[[(4R)-4-[(3R,5 S,7R,8R,9S,10S,12S,13R,14S,17R)-3,7,12-trihydroxy-10, 13-dimethyl-2,3,4,5,6,7,8,9,11,12,14,15,16,17-tetradecahydro-1H-cyclopenta[a]phenanthren-17-yl]pentanoyl]amino]ethanesulfonic acid; CAS No.: 81-24-3), taurodeoxycholic acid (2-(((3alpha,5beta, 12alpha)-3,12-dihydroxy-24-oxocholan-24-yl)amino)-ethanesulfonic acid; CAS No.: 516-50-7), ursocholic acid (3alpha,7beta, 12alpha-trihydroxy-5beta-cholan-24-oic acid; CAS: 2955-27-3), ursodeoxycholic acid (3 alpha,7beta-dihydroxy-5beta-cholan-24-oic acid; CAS: 128-13-2), and vulpecholic acid (1 alpha,3 alpha,7alpha-trihydroxy-5beta-cholan-24-oic acid; CAS: 107368-95-6) or a combination thereof.

3. The method of claim 1, wherein the conjugated bile acid (a) is the taurine or glycine conjugate of a bile acid.

4. The method of claim 1, wherein the bile acid is or comprises a taurodeoxycholic acid (2-(((3alpha,5beta, 12alpha)-3,12-dihydroxy-24-oxocholan-24-yl)amino)-ethanesulfonic acid; CAS No.: 516-50-7).

5. The method of claim 1, wherein the bile salt is or comprises a sodium taurodeoxycholate (CAS No.: 1180-95-6).

6. The method of claim 1, wherein the conjugated bile acid is or comprises taurodeoxycholate.

7. The method of claim 1, wherein the bile salt comprises a bile acid and a cation selected from the group consisting of an alkali metal, alkaline earth metal, transition metal, ammonium, amine and a quaternary ammonium.

8. The method of claim 1, wherein the sucralfate-bile interaction is binding of bile acid, bile salt or conjugated bile acid or a combination thereof by sucralfate.

9. The method of claim 8, wherein the binding is in vitro binding.

10. The method of claim 1, wherein the interaction is adsorption of bile acid, bile salt or conjugated bile acid or a combination thereof to sucralfate.

11. The method of claim 1, wherein the mammalian epithelial cells are a human intestinal epithelial cells.

12. The method of claim 11, wherein the human intestinal epithelial cell is Caco-2.

13. The method of claim 1, wherein the NSAID is selected from the group consisting of aceclofenac, acetyl salicylic acid, choline magnesium salicylate, clonixin, diflunisal, magnesium salicylate, salicyclic acid, salicylate, salsalate, sodium salicylate, dexibuprofen, dexketoprofen, diclofenac, droxicam, etodolac, fenoprofen, flufenamic acid, flurbiprofen, indomethacin, isoxicam, ketoprofen, ketorolac, lomoxican, loxoprofen, meclofenamate, meclofenamic acid, mefenamic acid, meloxicam, naproxen, nabumetone, oxaprozin, phenylbutazone, piroxicam, sulindac, tenoxicam, tolfenamic acid, tolmetin, ibuprofen, Cox-2 inhibitors and tramadol.

14. The method of claim 13, wherein the NSAID is indomethacin.

15. The method of claim 1, wherein the nonselective inhibitor of cyclooxygenase (COX) 1 and 2 is selected from the group consisting of asprin, diclofenac, ibuprofen, naproxen, mefenamic acid, indomethacin, ketoprofen and piroxicam and equivalents thereof.

16. The method of claim 1, wherein the values in (a) and (b) for the sucralfate suspension sample are obtained from multiple measurements of a single lot of sucralfate suspension sample or measurements from multiple lots of sucralfate suspension sample or a combination thereof.

17. The method of claim 1, wherein the reference values of (a) for the sucralfate suspension RLD is the range of about 7.08 to about 16.14 or a RLD SCFeq value range based on 90% confidence interval of about 5.34 to 18.486 mg/mL.

18. The method of claim 1, wherein the reference values of (b) for the sucralfate suspension RLD is a TEER range of about 23.3% to about 74.8%, wherein 100% TEER is the value of a control sample not treated with a Non-Steroidal Anti-Inflammatory Drug (NSAID) or a nonselective inhibitor of cyclooxygenase (COX) 1 and 2 at or about start of experiment (T=0).

19. The method of claim 1, wherein the reference values of (b) for the sucralfate suspension RLD has a TEER range of about 64.3% to about 92.5%, wherein 100% TEER is the value of a control sample not treated with a Non-Steroidal Anti-Inflammatory Drug (NSAID) or a nonselective inhibitor of (COX) 1 and 2 at or about start of experiment (T=0).

20. The method of claim 1, wherein the values are statistical means and the means of the values determined in (a) and (b) for the sucralfate suspension sample fall within three standard deviations of the means determined for the set of reference values set in (a) and (b) for the sucralfate RLD, respectively.

21. A method for determining in vitro bioequivalence of a sucralfate suspension sample to a sucralfate suspension RLD comprising:
  a. contacting the sucralfate suspension sample with a bile acid, bile salt and/or a conjugated bile acid or a combination thereof, so as to permit sucralfate-bile interaction, quantifying the interaction so as to obtain quantified values of the interaction and comparing said values to reference values for the sucralfate suspension RLD; and
  b. contacting the sucralfate suspension sample with a cell culture system in the presence of a Non-Steroidal Anti-Inflammatory Drug (NSAID) or a nonselective inhibitor of cyclooxygenase (COX) 1 and 2 so as to inhibit cell damage induced by the NSAID or nonselective inhibitor of COX 1 and 2 in the cell culture system, quantifying the cell damage so as to obtain quantified value(s) for the sucralfate suspension sample and comparing the said value(s) to reference values for the sucralfate suspension RLD, wherein the cell culture system comprises a monolayer of mammalian epithelial cells and the cell damage comprises loss of the cell monolayer's transepithelial electrical resistance (TEER);

wherein the reference values for the sucralfate suspension RLD in step (a) are derived from a set of values obtained from quantifying the sucralfate-bile interaction for 2 or more lots of the sucralfate suspension RLD; wherein sucralfate-bile interaction is interaction between sucralfate and bile acid, bile salt and/or conjugated bile acid or a combination thereof; and wherein the sucralfate suspension sample is to have said in vitro bioequivalence to a sucralfate suspension RLD when the values determined in (a) and (b) for the sucralfate suspension sample are within the reference values in (a) and (b) for the sucralfate suspension RLD, respectively, and wherein the reference values in (a) and (b) for the sucralfate suspension RLD are experimentally determined values characterized by a minimum and a maximum value and in vitro bioequivalence includes no less than about 80% of the values in (a) and (b) for the sucralfate suspension sample to be within the range of reference values in (a) and (b), respectively.

22. A method for determining in vitro bioequivalence of a sucralfate suspension sample to a sucralfate suspension RLD comprising:
   a. contacting the sucralfate suspension sample with a bile acid, bile salt and/or a conjugated bile acid or a combination thereof, so as to permit sucralfate-bile interaction, quantifying the interaction so as to obtain quantified values of the interaction and comparing said values to reference values for the sucralfate suspension RLD; and
   b. contacting the sucralfate suspension sample with a cell culture system in the presence of a Non-Steroidal Anti-Inflammatory Drug (NSAID) or a nonselective inhibitor of cyclooxygenase (COX) 1 and 2 so as to inhibit cell damage induced by the NSAID or nonselective inhibitor of COX 1 and 2 in the cell culture system quantifying the cell damage so as to obtain quantified value(s) for the sucralfate suspension sample and comparing the said value(s) to reference values for the sucralfate suspension RLD, wherein the cell culture system comprises a monolayer of mammalian epithelial cells and the cell damage comprises loss of the cell monolayer's transepithelial electrical resistance (TEER);
   wherein the reference values for the sucralfate suspension RLD in step (a) are derived from a set of values obtained from quantifying the sucralfate-bile interaction for 2 or more lots of the sucralfate suspension RLD; wherein sucralfate-bile interaction is interaction between sucralfate and bile acid, bile salt and/or conjugated bile acid or a combination thereof; and wherein the sucralfate suspension sample is to have said in vitro bioequivalence to a sucralfate suspension RLD when the values determined in (a) and (b) for the sucralfate suspension sample are within the reference values in (a) and (b) for the sucralfate suspension RLD, respectively, wherein the reference values in (a) and (b) for the sucralfate suspension RLD are experimentally determined values characterized by a minimum and a maximum value and in vitro bioequivalence requires the values in (a) and (b) for the sucralfate suspension sample to be within the range of reference values in (a) and (b), respectively.

23. A method for determining in vitro bioequivalence of a sucralfate suspension sample to a sucralfate suspension RLD comprising:
   a. contacting the sucralfate suspension sample with a bile acid, bile salt and/or a conjugated bile acid or a combination thereof, so as to permit sucralfate-bile interaction, quantifying the interaction so as to obtain quantified values of the interaction and comparing said values to reference values for the sucralfate suspension RLD; and
   b. contacting the sucralfate suspension sample with a cell culture system in the presence of a Non-Steroidal Anti-Inflammatory Drug (NSAID) or a nonselective inhibitor of (COX) 1 and 2 so as to inhibit cell damage induced by the NSAID or nonselective inhibitor of COX 1 and 2 in the cell culture system, quantifying the cell damage so as to obtain quantified value(s) for the sucralfate suspension sample and comparing the said value(s) to reference values for the sucralfate suspension RLD, wherein the cell culture system comprises a monolayer of mammalian epithelial cells and the cell damage comprises loss of the cell monolayer's transepithelial electrical resistance (TEER);
   wherein the reference values for the sucralfate suspension RLD in step (a) are derived from a set of values obtained from quantifying the sucralfate-bile interaction for 2 or more lots of the sucralfate suspension RLD; wherein sucralfate-bile interaction is interaction between sucralfate and bile acid, bile salt and/or conjugated bile acid or a combination thereof; and wherein the sucralfate suspension sample is to have said in vitro bioequivalence to a sucralfate suspension RLD when the values determined in (a) and (b) for the sucralfate suspension sample are within the reference values in (a) and (b) for the sucralfate suspension RLD, respectively, and wherein the sucralfate suspension sample is said to have in vitro bioequivalence to a sucralfate suspension RLD when (i) the value determined in quantifying the sucralfate-bile interaction of the sucralfate suspension sample with a bile acid, bile salt and/or conjugated bile acid or a combination thereof is within the 90% confidence interval range of a set of SCFeq values obtained from quantifying the sucralfate-bile interaction for 2 or more lots of the sucralfate suspension RLD; (ii) TEER values determined in quantifying the cell damage of the sucralfate suspension sample with a cell culture system is within the 90% confidence interval range of the set of values obtained from quantifying the cell damage for 2 or more lots of the sucralfate suspension RLD; (iii) ratio of mean of the values (Mean of the Test/Mean of the RLD) determined in quantifying the sucralfate-bile interaction of the sucralfate suspension sample with a bile acid, bile salt and/or bile conjugate base or a combination thereof to the mean of the set of values obtained from quantifying the sucralfate-bile interaction for 2 or more lots of the sucralfate suspension reference listed drug is within the range of about 0.80 to 1.25; and (iv) ratio of mean of the values determined in quantifying the cell damage of the sucralfate suspension sample with a cell culture system to the mean of the set of values obtained from quantifying the cell damage for 2 or more lots of the sucralfate suspension reference listed drug is within the range of about 0.80 to 1.25; and (v) the 90% confidence interval is a range of values within 1.5 standard deviations about the mean of values measured for two or more lots of the Sucralfate suspension RLD.

* * * * *